(12) United States Patent
Jinno et al.

(10) Patent No.: US 8,137,339 B2
(45) Date of Patent: Mar. 20, 2012

(54) WORKING MECHANISM AND MANIPULATOR

(75) Inventors: Makoto Jinno, Ota-ku (JP); Takamitsu Sunaoshi, Yokohama (JP); Shigeru Omori, Ashigarakami-gun (JP)

(73) Assignees: Terumo Kabushiki Kaisha, Tokyo (JP); Kabushiki Kaisha Toshiba, Tokyo (JP)

( * ) Notice: Subject to any disclaimer, the term of this patent is extended or adjusted under 35 U.S.C. 154(b) by 708 days.

(21) Appl. No.: 11/832,872

(22) Filed: Aug. 2, 2007

(65) Prior Publication Data

US 2008/0039255 A1 Feb. 14, 2008

(30) Foreign Application Priority Data

Aug. 8, 2006 (JP) .................................. 2006-215901

(51) Int. Cl.
*A61B 17/00* (2006.01)
(52) U.S. Cl. ............................................. 606/1; 474/148
(58) Field of Classification Search ...................... 606/1
See application file for complete search history.

(56) References Cited

U.S. PATENT DOCUMENTS

| | | | | |
|---|---|---|---|---|
| 3,631,737 A | * | 1/1972 | Wells ............................... | 74/469 |
| 4,353,677 A | * | 10/1982 | Susnjara et al. ............... | 414/735 |
| 4,762,016 A | * | 8/1988 | Stoughton et al. ......... | 74/490.01 |
| 5,046,375 A | * | 9/1991 | Salisbury et al. ............. | 74/89.22 |
| 5,431,645 A | * | 7/1995 | Smith et al. ......................... | 606/1 |
| 5,514,157 A | | 5/1996 | Nicholas et al. | |
| 5,792,165 A | * | 8/1998 | Klieman et al. ............... | 606/170 |
| 5,797,900 A | | 8/1998 | Madhani et al. | |
| 6,371,952 B1 | * | 4/2002 | Madhani et al. ................... | 606/1 |
| 6,676,684 B1 | * | 1/2004 | Morley et al. ................. | 606/205 |
| 6,695,774 B2 | * | 2/2004 | Hale et al. ...................... | 600/173 |
| 6,889,116 B2 | | 5/2005 | Jinno | |
| 2002/0040217 A1 | * | 4/2002 | Jinno ................................. | 606/1 |
| 2003/0100892 A1 | | 5/2003 | Morley et al. | |
| 2004/0266574 A1 | | 12/2004 | Jinno et al. | |
| 2006/0167589 A1 | | 7/2006 | Jinno | |

FOREIGN PATENT DOCUMENTS

| | | |
|---|---|---|
| EP | 1 679 046 A2 | 7/2006 |
| EP | 1 707 153 A1 | 10/2006 |
| JP | 4-310391 | 11/1992 |
| JP | 2001-277157 | 10/2001 |
| JP | 2002-102248 | 4/2002 |
| JP | 2004-301275 | 10/2004 |

OTHER PUBLICATIONS

Japanese Office Action issued on Feb. 8, 2011, in the corresponding Japanese Patent Application No. 2006-215901 (with the English Translation of pertinent portion).

* cited by examiner

*Primary Examiner* — Aaron Roane
(74) *Attorney, Agent, or Firm* — Oblon, Spivak, McClelland, Maier & Neustadt, L.L.P.

(57) ABSTRACT

A working unit includes a gear body disposed forwardly of a tubular member around which a wire is wound and having a rotational axis disposed substantially parallel to the tubular member, and a first gear and a second gear for transmitting rotation of a gear body to another gear body. The numbers of turns of wires, the size of a main shaft, and the size of a gear body, which are positioned forwardly of the tubular member, have no adverse effect on the manner in which a wire is wound around the tubular member. The wire can be wound around the tubular member over a wide region thereof for increasing the angular displacement of the gear body. The increased angular displacement of the gear body makes it possible to increase the angular displacement and rotational torque of the gear body.

8 Claims, 22 Drawing Sheets

WORKING MECHANISM AND MANIPULATOR

BACKGROUND OF THE INVENTION

1. Field of the Invention

The present invention relates to a working mechanism for operating at least one joint shaft of a working unit by rotating pulleys based on circulative rotation of flexible power transmitting members such as wires or the like wound around the pulleys, and a manipulator having such a working mechanism on its distal end for performing manipulating actions from the other end thereof through an arm or the like.

2. Description of the Related Art

According to laparoscopic surgery, it is customary to form a plurality of holes in the abdominal part of the patient, insert an endoscope and a manipulator (or forceps) into the respective holes, and perform the surgical operation while images captured by the endoscope are being observed on a display monitor by the surgeon. Since such a laparoscopic surgical operation does not require the abdominal cavity to be opened, the burden on the patient is small and the number of days which the patient needs to recover and spend in the hospital until they are allowed to come out of hospital is greatly reduced. For these reasons, the laparoscopic surgical operation is expected to find an increased range of applications.

Manipulators for use in laparoscopic surgery are desirably capable of quick and appropriate surgical techniques depending on the position and size of the affected region, and are used to perform various surgical techniques like suture, ligature, knot-tying and removing of the affected part of the patient. The present applicant has developed and proposed manipulators which have a high degree of freedom for manipulation and which can easily be operated (see, for example, Japanese Laid-Open Patent Publication No. 2002-102248 and Japanese Laid-Open Patent Publication No. 2004-301275). This application claims priority to Japanese Laid-Open Patent Puublication No. 2006-215901.

SUMMARY OF THE INVENTION

It is an object of the present invention to provide a working mechanism having increased movable ranges, reliability, and ease with which it operates, and a manipulator incorporating such a working mechanism.

A working mechanism according to the present invention comprises a first flexible power transmitting member, a first tubular member, the first flexible power transmitting member being wound around the first tubular member, the first tubular member being rotatable about its own axis, a second flexible power transmitting member disposed substantially parallel to the first flexible power transmitting member and extending in sandwiching relation to the first tubular member, a second tubular member having a rotational axis extending substantially parallel to the first tubular member, the second flexible power transmitting member being wound around the second tubular member, a driven rotor having a rotational axis extending substantially parallel to the first tubular member, a first rotation transmitting mechanism for transmitting rotation of the first tubular member to the driven rotor, a first working unit operable in ganged relation to rotation of the driven rotor, and a second working unit operable in ganged relation to rotation of the second tubular member.

A manipulator according to the present invention comprises a first input member and a second input member, a first rotational source and a second rotational source which are rotatable in response to operation of the first input member and the second input member, a first flexible power transmitting member including a rear portion wound around the first rotational source and a front portion wound in a plurality of turns around a first tubular member, a second flexible power transmitting member disposed substantially parallel to the first flexible power transmitting member and extending forwardly on both sides of the first rotational source, the second flexible power transmitting member including a rear portion wound around the second rotational source, the second flexible power transmitting member being wound around a second tubular member disposed in front of the first tubular member, a driven rotor disposed in front of the first tubular member and having a rotational axis disposed substantially parallel to the first tubular member, a rotation transmitting mechanism for transmitting rotation of the first tubular member to the driven rotor, a first working unit operable in ganged relation to rotation of the driven rotor, and a second working unit operable in ganged relation to rotation of the second tubular member.

With the working mechanism and the manipulator according to the present invention, the number of turns of the second flexible power transmitting member and the size of the second tubular member have no adverse effect on the manner in which the first flexible power transmitting member is wound around the first tubular member. Therefore, the first flexible power transmitting member can be wound around the first tubular member over a wide region thereof for increasing the angular displacement of the first tubular member. The angular movement and rotational torque of the driven rotor can thus be increased to enlarge the movable range and improve the operability of the working mechanism and the manipulator.

The working mechanism and the manipulator according to the present invention are simple in structure and high in reliability.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 21:
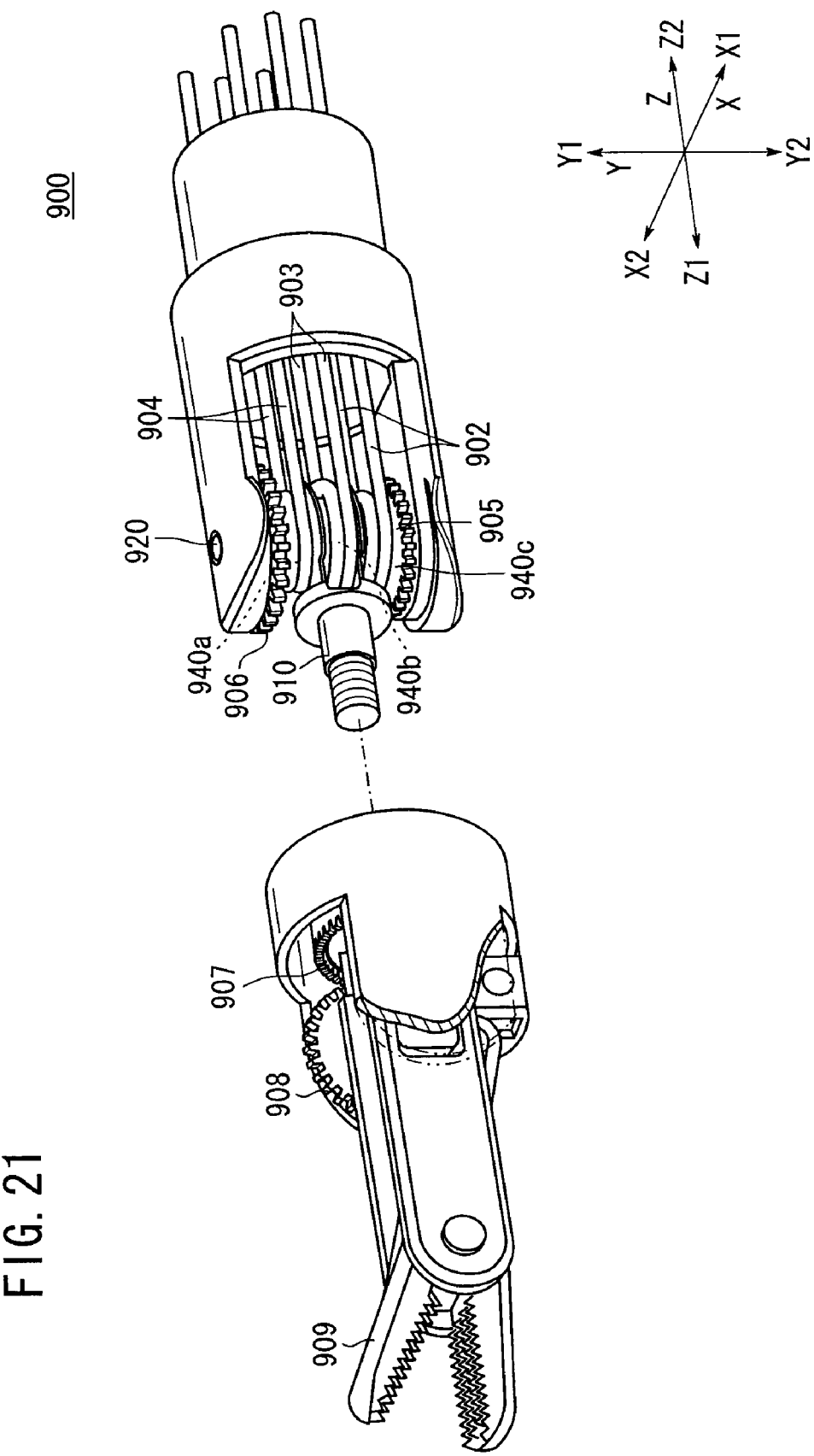
FIG. 21 is an exploded perspective view of a working unit.

The applicant has also developed a working unit 900 shown in FIG. 21 of the accompanying drawings in relation to the manipulators.

As shown in FIG. 21, the working unit 900 is actuated by a wire 902, a wire 903, and a wire 904 and has three degrees of freedom. The wires 902, 903, 904 are wound around respective tubular bodies 940c, 940b, 940a.

In the working unit 900, the wires 902, 904 are operated to rotate a gear 905, which rotates a face gear, not shown, to rotate the distal end of the working unit 900 in a rolling direction. The wire 904 is operated to rotate a second gear 906, which causes a gear ring 907 and a gear 908 to open and close a gripper 909. The wires 902, 903, 904 are operated to cause a main shaft 910 to rotate the distal end in a yawing direction.

The working unit 900 is of a diameter small enough to be inserted into a small-diameter trocar that is placed in the abdominal part or the like of the patient. If the working unit 900 is too large in diameter, then the hole into which it is to be inserted has to be correspondingly large in diameter, resulting in a failure to reduce the burden on the patient.

Figure 22A:
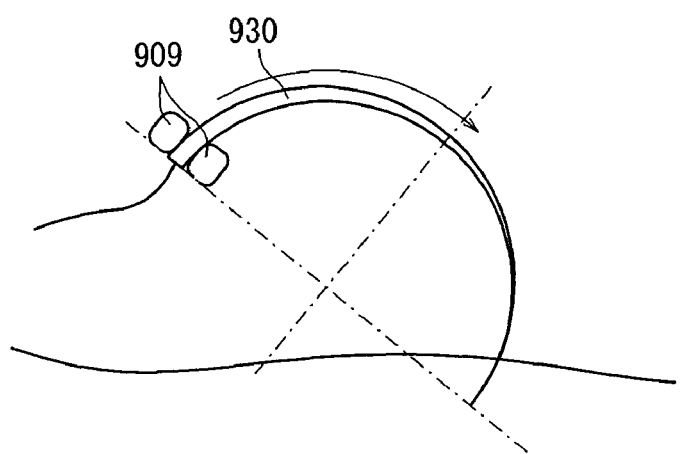
FIG. 22A is a view showing the manner in which a curved needle held by a gripper is about to be inserted into a living tissue.
Figure 22B:
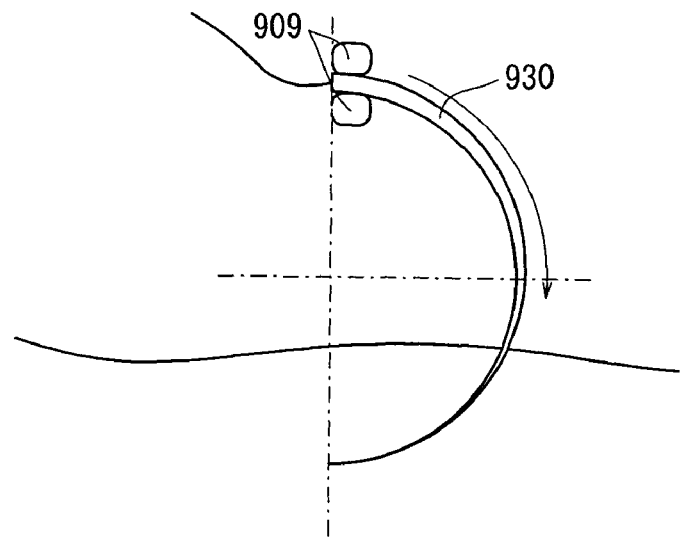
FIG. 22B is a view showing the manner in which the curved needle held by the gripper is inserted into the living tissue.
Figure 22C:
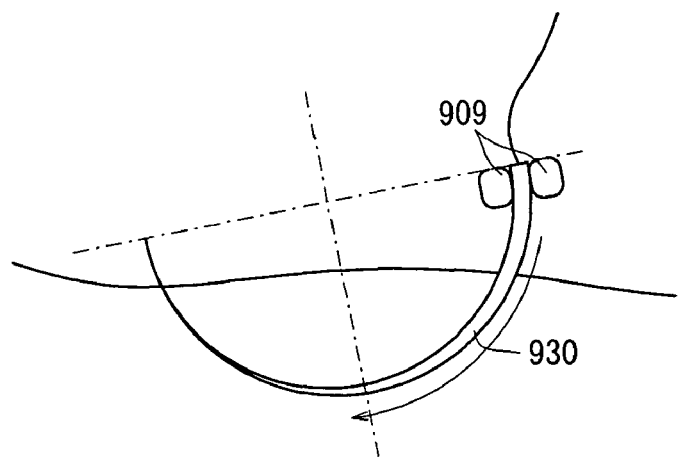
FIG. 22C is a view showing the manner in which the curved needle held by the gripper is inserted into the living tissue and has its tip exposed from the living tissue.

If the working unit 900 has degrees of freedom that involve a yaw axis and a pitch axis, then the working unit 900 does not require a large operating range as it is ±90°. However, if the working unit 900 operates also about a roll axis, then its operating range about the roll axis greatly affects the ease with which the working unit 900 operates. For example, as shown in FIGS. 22A through 22C, when a living tissue is sutured by a curved needle 930 held by a gripper 909, it is desirable for the working unit 900 to have an operating range of ±180° or greater around the roll axis in order to allow the curved needle 930 to be smoothly inserted into and taken out of the living tissue at a desired posture.

Increasing the operating range requires that as many turns as possible of the wires 902, 903, 904 be placed around the tubular bodies 940a, 940b, 940c. However, since the wires 902, 903, 904 are wound as juxtaposed turns coaxially around a support shaft 920 and there is no sufficient space around the support shaft 920, it is difficult to increase the number of turns of the wires 902, 903, 904.

For example, in the working unit 900 shown in FIG. 21, each of the wires 902, 903, 904 has 1.5 turns (540°) around one of the tubular bodies 940a, 940b, 940c. Because of the limited space around the support shaft 920, it is difficult to increase the angle through which the wires 902, 903, 904 are wound around the tubular bodies 940a, 940b, 940c, i.e., the wire winding angle. In other words, if a greater number of turns of the wires 902, 903, 904 are to be wound, and then the support shaft 920 has to be longer, resulting in a larger diameter of the working unit 900.

If the working unit 900 has an operating range of ±90° about the yaw axis and an operating range of ±180° about the roll axis, then the wire winding angle is already 540° for operating the working unit 900 about the yaw axis and the roll axis, and there is no further wire winding angle available for wire turns for causing the working unit 900 to make a gripping action. Stated otherwise, in order for the working unit 900 to make a gripping action, the operating range about the yaw axis or the operating range about the roll axis has to be reduced.

In view of the above-mentioned problems, an object of the present invention is to provide a working mechanism having increased movable ranges, reliability and operability, and a manipulator incorporating such a working mechanism.

Working mechanisms and manipulators according to first, second, and third embodiments of the present invention will be described below with reference to FIGS. 1 through 20. A manipulator 10a (see FIG. 1) according to a first embodiment, a manipulator 10b (see FIG. 12) according to a second embodiment, and a manipulator 10c (see FIG. 17) according to a third embodiment are typically in the form of medical manipulators for use in laparoscopic surgical operations or the like. Working units (working mechanisms) 12a, 12b, 12c according to the first, second, and third embodiments comprise mechanisms having three degrees of freedom and mounted on the distal ends of the manipulators 10a, 10b, 10c.

The working unit 12a mounted on the distal end of the manipulator 10a serves to grip a portion of a living tissue, a curved needle, or the like for performing a certain operation, and is usually referred to as gripping forceps or a needle driver (needle holder).

Figure 1:
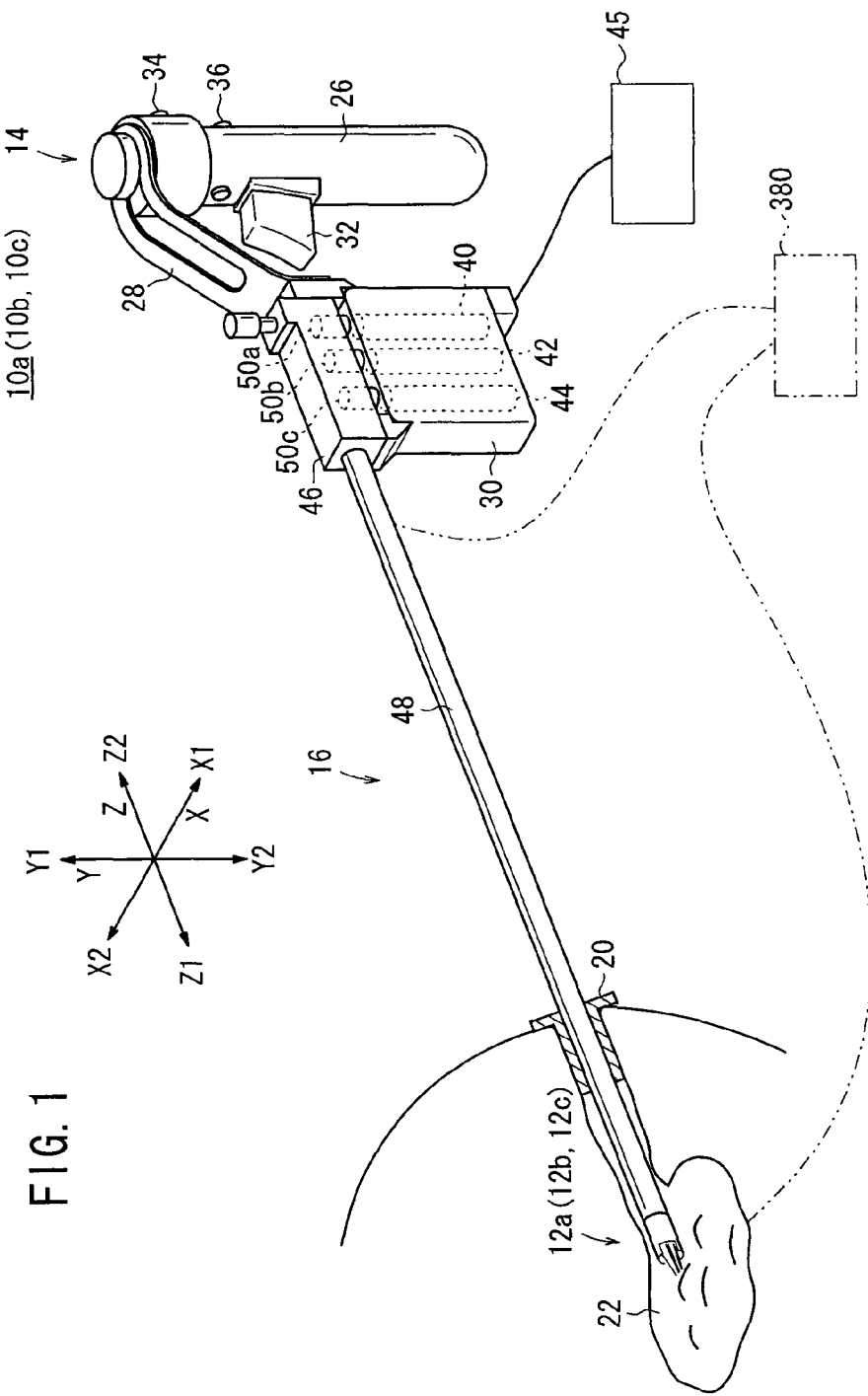
FIG. 1 is a perspective view of a manipulator according to a first embodiment of the present invention.

As shown in FIG. 1, the manipulator 10a comprises an operation command unit 14 on a proximal end thereof which is held and operated by hand, the working unit 12a on the distal end thereof for working on a living tissue, and an elongate connector 16 interconnecting the working unit 12a and the operation command unit 14. The working unit 12a and the connector 16 are of a small diameter and can be inserted into a body cavity 22 through a trocar 20 in the form of a hollow cylinder mounted in an abdominal region or the like of the patient. The working unit 12a is actuated by the operation command unit 14 to perform various techniques to remove, grip, suture, or tie an affected part of the patient's body in the body cavity 22.

Figure 12:
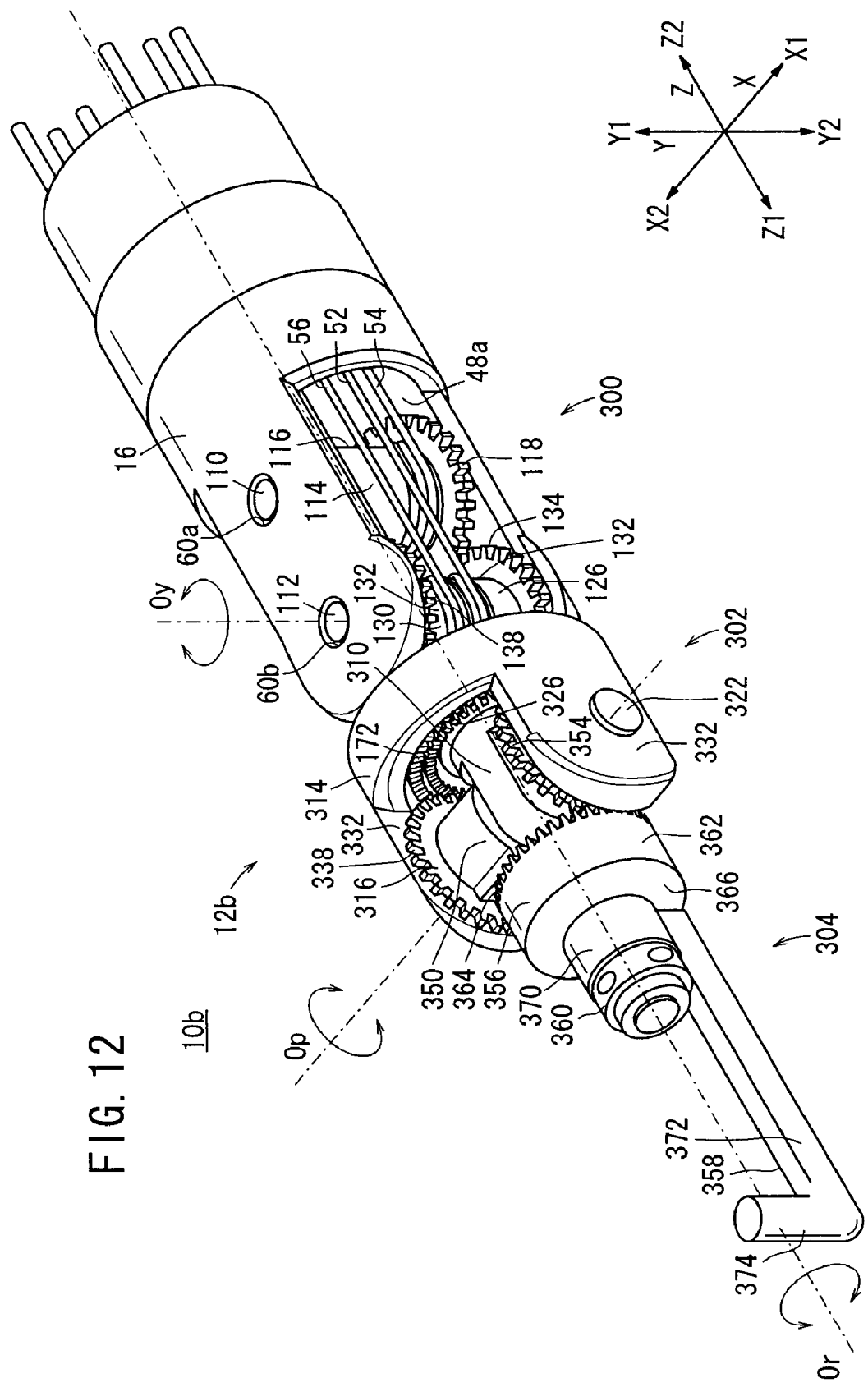
FIG. 12 is a perspective view of a working unit according to a second embodiment of the present invention.
Figure 17:
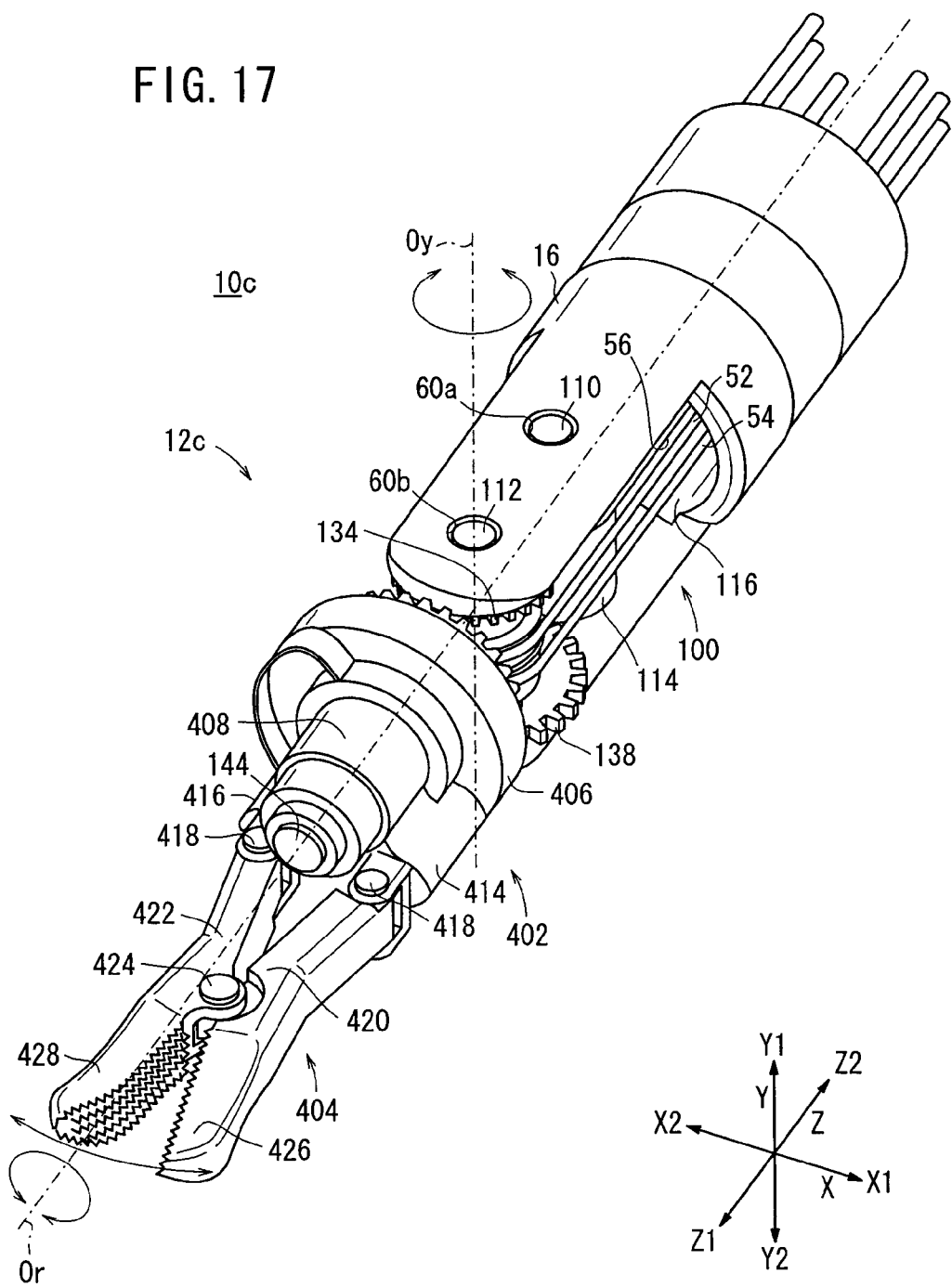
FIG. 17 is a perspective view of a working unit according to a third embodiment of the present invention.

It is assumed in the description which follows that the transverse direction of each of the manipulators 10a, 10b, 10c is referred to as X direction, vertical direction thereof as Y direction, and longitudinal directions of the connector 16 as Z direction in FIGS. 1, 12, and 17. Of the X directions, the rightward direction is referred to as an X1 direction, and the leftward direction as an X2 direction. Of the Y directions, the upward direction is referred to as a Y1 direction, and the downward direction as a Y2 direction. Of the Z directions, the forward direction is referred to as a Z1 direction, and the rearward direction as a Z2 direction. Unless otherwise noted, these directions represent directions of the manipulators 10a, 10b, 10c when they are of a neutral posture (shown in FIGS. 2, 12, and 17). The definition of the above directions is for illustrative purpose only, and the manipulators 10a, 10b, 10c can be used in any orientations, e.g., it may be used upside down.

The operation command unit 14 includes a grip handle 26 gripped by hand, an arm 28 extending from an upper portion of the grip handle 26, and an actuator block 30 connected to a distal end of the arm 28. The grip handle 26 includes a trigger lever (first input member) 32, a first instruction lever (second input member) 34, and a second instruction lever 36 which are operable by a finger. The trigger lever 32 is disposed in a position where it can easily be pulled by an index finger.

The actuator block 30 houses therein three motors 40, 42, 44 corresponding to respective mechanisms of three degrees of freedom which are incorporated in the working unit 12a. The motors 40, 42, 44 are arrayed parallel to each other in the longitudinal direction of the connector 16. The motors 40, 42, 44 are small in size and diameter, making the actuator block 30 compact and flat in shape. The actuator block 30 is disposed downwardly of the end of the operation command unit 14 in the Z1 direction. The motors 40, 42, 44 rotate under the control of a controller 45 based on the operation of the operation command unit 14.

The connector 16 includes a joint 46 joined to the actuator block 30 and a hollow connector shaft 48 extending in the Z1 direction from the joint 46. The joint 46 houses therein a drive pulley (second rotational source) 50a, a drive pulley 50b, and a drive pulley (first rotational source) 50c which are rotatable and are connected respectively to the drive shafts of the motors 40, 42, 44. A wire (second flexible power transmitting member) 52, a wire 54, and a wire (first flexible power transmitting member) 56 (see FIG. 2) are trained respectively around the drive pulleys 50a, 50b, 50c and extend through a space 48a in the connector shaft 48 to the working unit 12a. The wires 52, 54, 56 may be of the same type and same diameter. The wires 52, 54, 56 will collectively be referred to as a wire 57.

The joint 46 can be operated according to a predetermined process to disconnect the connector 16 from the operation command unit 14 for cleaning, sterilization, maintenance, etc. The connector 16 and the working unit 12a can be replaced with other connectors and working units. For example, depending on the technique required for a certain surgical operation, the connector 16 may be replaced with a connector having a different length and/or the working unit 12a may be replaced with a working unit incorporating different mechanisms.

Figure 2:
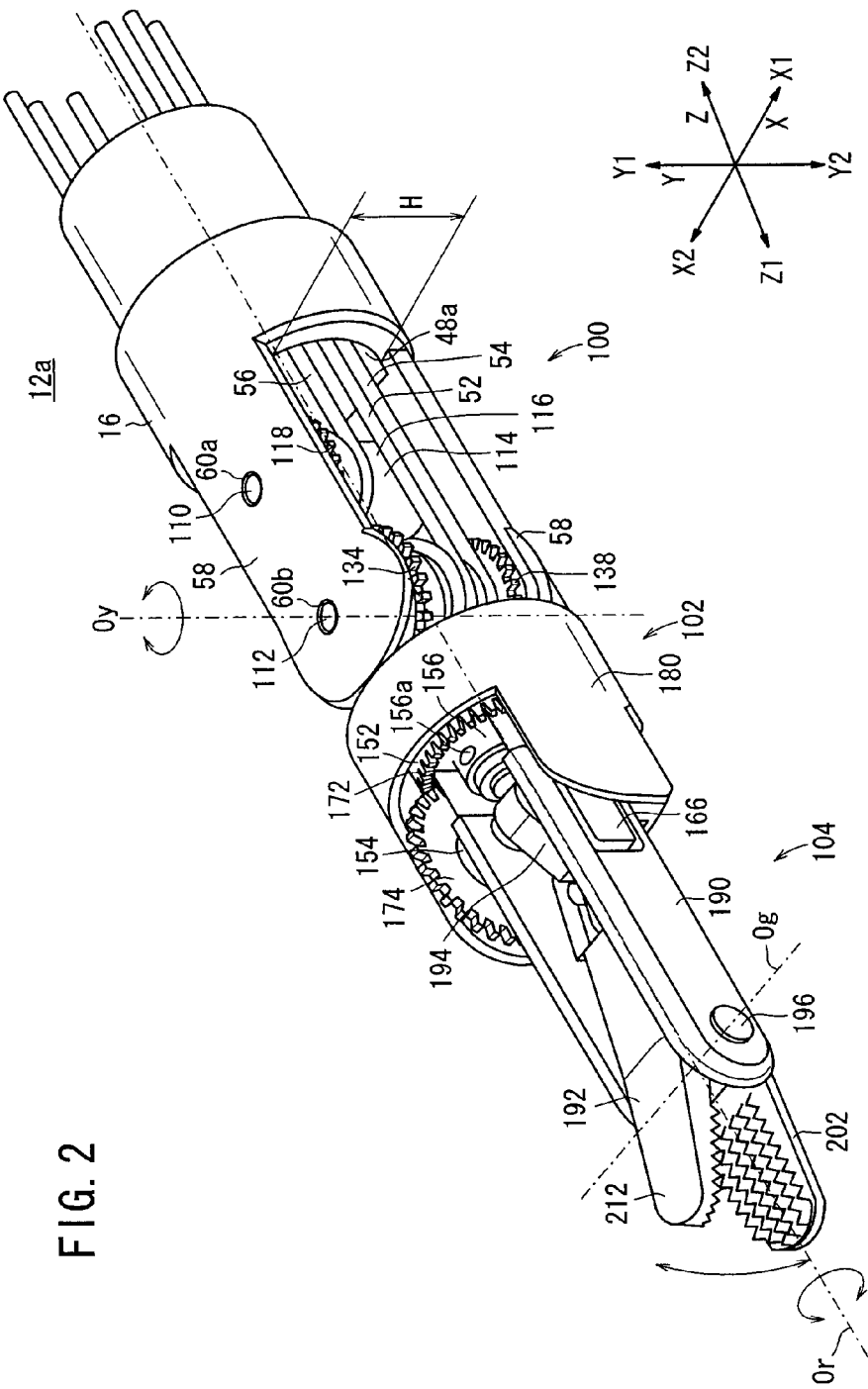
FIG. 2 is a perspective view of a working unit (working mechanism) according to the first embodiment.
Figure 3:
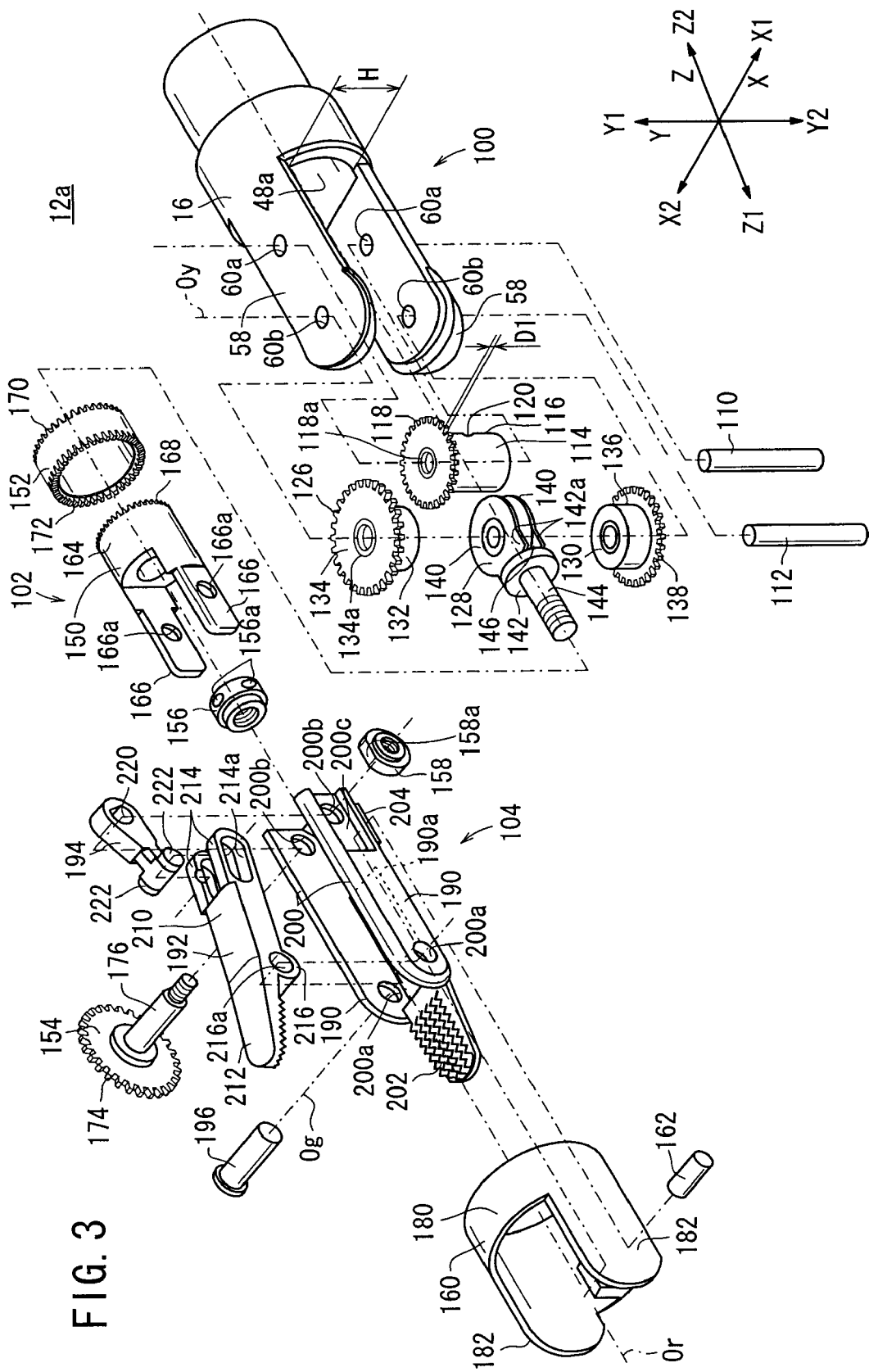
FIG. 3 is an exploded perspective view of the working unit according to the first embodiment.
Figure 4:
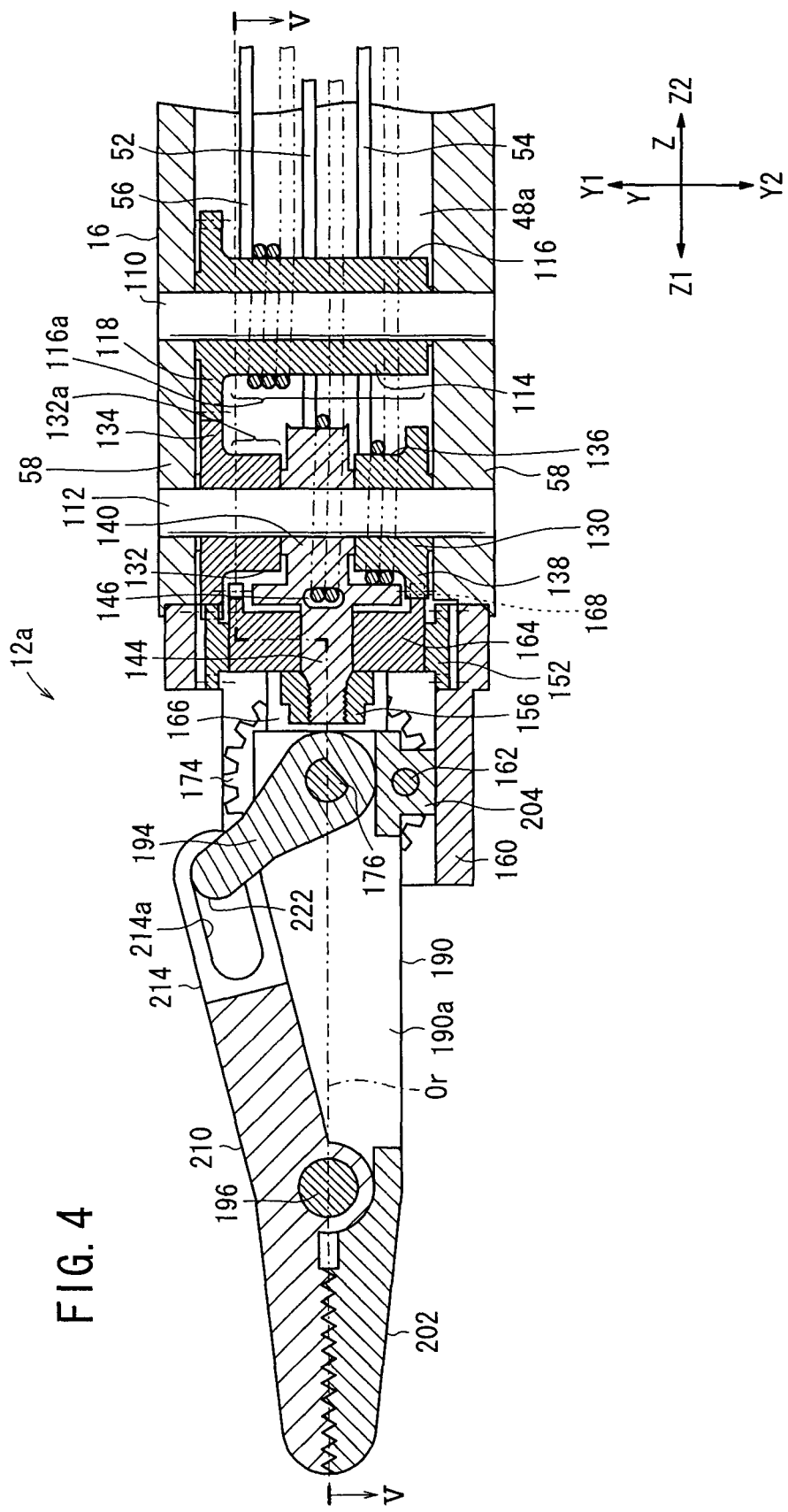
FIG. 4 is a sectional side elevational view of the working unit according to the first embodiment.

As shown in FIG. 2, the connector 16 has a pair of diametrically opposite tongues 58 projecting toward the distal end thereof and disposed in facing relation to the central axis of the connector shaft 48. The space 48a in the connector shaft 48 communicates with a space between the tongues 58. The tongues 58 have two axially spaced pairs of shaft holes 60a, 60b defined respectively therein which are held in alignment with each other. The tongues 58 have respective distal ends which are in arc shapes. The pair of tongues 58 has respective flat inner surfaces facing each other which extend parallel to each other and which are spaced from each other by a distance H.

The two shaft holes 60a and the two shaft holes 60b are disposed one on each side of the central axis of the connector 16. The shaft holes 60a, 60b are juxtaposed along the Z directions, and the shaft holes 60b are closer to the distal ends of the tongues 58 than the shaft holes 60a.

As shown in FIG. 2, the working unit 12a incorporates therein mechanisms of three degrees of freedom. These mechanisms include a mechanism having a first degree of freedom for angularly moving a portion of the working unit 12a that is positioned ahead of a first rotational axis Oy extending along the Y directions, in yawing directions about the first rotational axis Oy, a mechanism having a second degree of freedom for angularly moving the portion of the working unit 12a in rolling directions about a second rotational axis Or extending along the Z directions, and a mechanism having a third degree of freedom for opening and closing an end effector 104 on the distal end of the working unit 12a about a third rotational axis Og extending along the X directions. The working unit 12a comprises a wire-driven mechanism 100, a drive mechanism 102, and the end effector 104. Though the drive mechanism 102 and the end effector 104 will hereinafter be described separately from each other for convenience, since the term "end effector" is generally interpreted as a mechanism on an arm end for performing a certain action, the end effector 104 and the drive mechanism 102 may be defined as an integrated end effector.

The wire-driven mechanism 100, the drive mechanism 102, and the end effector 104 will be described in detail below with reference to FIGS. 2 through 5.

The wire-driven mechanism 100 is disposed between the tongues 58 and serves to convert circulative movements of the respective wires 52, 54, 56 into rotational movements and transmit the rotational movements to the drive mechanism 102. The wire-driven mechanism 100 includes a shaft 110 inserted in the shaft holes 60a, a shaft 112 inserted in the shaft holes 60b, and a gear body 114 rotatably supported on the shaft 110. The shafts 110, 112 are press-fitted securely in the shaft holes 60a, 60b. The shaft 112 is axially aligned with the first rotational axis Oy.

The gear body 114 comprises a tubular member (first tubular member) 116 and a first gear (first rotation transmitting mechanism, joint drive gear) 118 disposed concentrically on an upper portion of the tubular member 116. The first gear 118 comprises a spur gear greater in diameter than the tubular member 116. Unless otherwise specified, a gear referred herein comprises a spur gear. The gear body 114 has a height which is substantially equal to the distance H and is rotatably disposed between the tongues 58. The first gear 118 has a thickness D1 sufficiently smaller than the height H, so that the height (H−D1) of the tubular member 116 takes up a substantial portion of the height H between the tongues 58. The first gear 118 has a low annular rib 118a disposed on the upper surface thereof around the hole through which the shaft 110 is inserted. The annular rib 118a prevents the upper surface of the first gear 118 from contacting the upper tongue 58, thereby reducing the sliding resistance that is imposed on the first gear 118 by the upper tongue 58.

Figure 6:
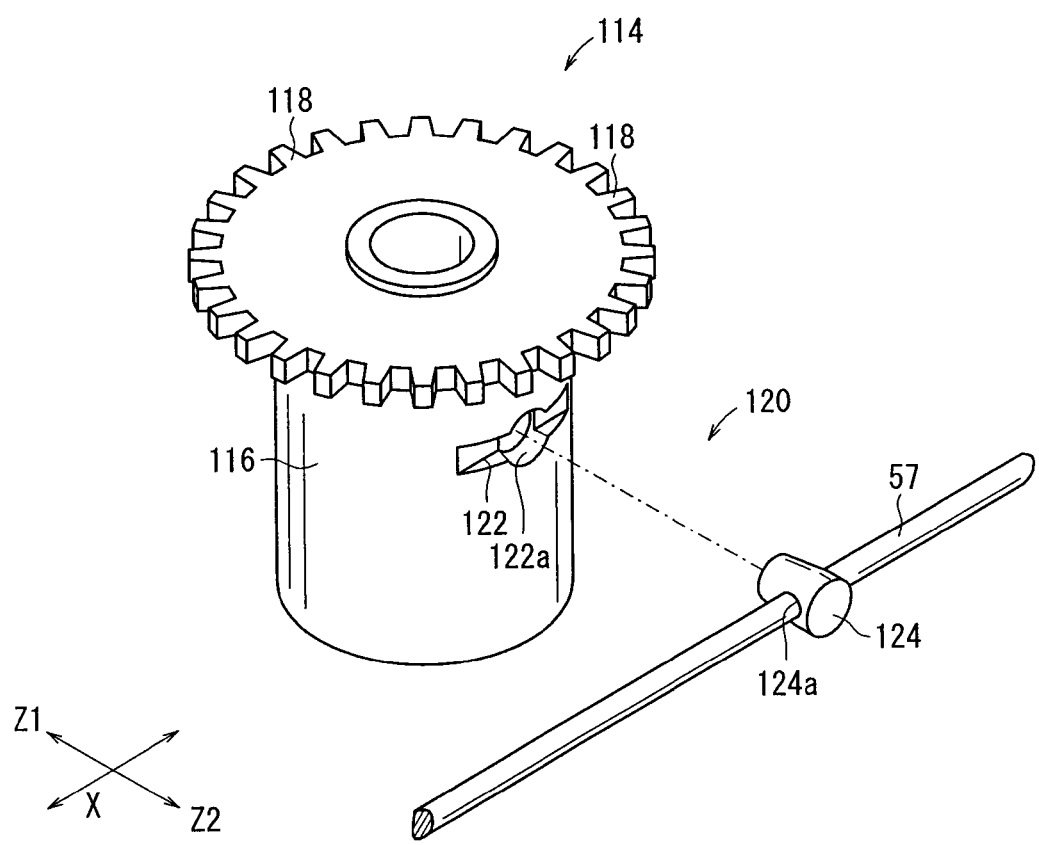
FIG. 6 is an exploded perspective view of a wire securing mechanism.

As shown in FIG. 6, the tubular member 116 is combined with a wire securing mechanism 120. The wire securing mechanism 120 has a groove 122 defined in an upper portion of the side of the tubular member 116 which faces the Z2 direction and extending laterally in the X directions when the gear body 114 is in a neutral position, and a tapered fastening pin 124 disposed centrally in the groove 122. The groove 122 has a recess 122a positioned at the center of the fastening pin 124 to be inserted and fixed therein. The groove 122 may be slightly inclined in alignment with a turn of the wire 57 that is helically wound around the tubular member 116.

The groove 122 has a width and a maximum depth that are essentially equal to the diameter of the wire 57. The fastening pin 124 has a hole 124a defined laterally therethrough for the wire 57 to extend therethrough. The wire 57 is threaded through the hole 124a and the fastening pin 124 is inserted into the recess 122a, holding the wire 57 partly in the groove 122. The wire 57 is thus oriented horizontally and fastened to the tubular member 116.

As shown in FIGS. 2 through 5, the wire-driven mechanism 100 comprises a gear body (driven rotor) 126, a main shaft 128, and a gear body 130, which are rotatably supported on the shaft 112 and arranged successively in the Y2 direction.

The gear body 126 comprises a tubular member 132 and a second gear (second rotation transmitting mechanism) 134 disposed concentrically on an upper portion of the tubular member 132. The second gear 134 has the same thickness as the first gear 118 and is held in mesh with the first gear 118. The second gear 134 has a greater number of teeth than the first gear 118, and hence can transmit the rotation of the first gear 118 at a lower speed (with a higher torque). Alternatively, the second gear 134 may be designed to transmit the rotation of the first gear 118 at the same speed or a higher speed. The second gear 134 has a low annular rib 134a disposed on the upper surface thereof around the hole through which the shaft 112 is inserted. The annular rib 134a prevents the upper surface of the second gear 134 from contacting the upper tongue 58, thereby reducing the sliding resistance that is imposed on the second gear 134 by the upper tongue 58.

The gear body 130 is essentially identical in shape to the gear body 126, but is in an upside-down orientation with respect to the gear body 126. The gear body 130 comprises a tubular member 136 and a third gear 138 disposed concentrically on a lower portion of the tubular member 136. The tubular member 136 is substantially identical in diameter and shape to the tubular member 132. The third gear 138 has a number of teeth which may be slightly smaller than the second gear 134. The tubular member 136 is combined with a wire securing mechanism 120, which is similar to the wire securing mechanism 120 of the tubular member 116, on the side of the tubular member 136 which faces the Z2 direction, and the wire 54 is fastened to the tubular member 136 by the wire securing mechanism 120.

The main shaft 128 has a tubular member (second tubular member) 140 through which the shaft 112 extends, an annular seat 142 coupled to the tubular member 140 and facing the Z1 direction, and a support bar 144 extending from the center of the annular seat 142 in the Z1 direction. The support bar 144 is axially aligned with the second rotational axis Or. The support bar 144 has an externally threaded distal end portion.

The annular seat 142 is slightly spaced from an outer side surface of the tubular member 140 with two upper and lower bridges 142a interposed therebetween. A vertical hole 146 which is slightly elongate in the Y directions is defined between the annular seat 142 and the tubular member 140 for receiving the wire 52 to extend therethrough. The tubular member 140 is combined with a wire securing mechanism 120, which is similar to the wire securing mechanism 120 of the tubular member 116, on the side of the tubular member 140 which faces the Z2 direction, and the wire 52 is fastened to the tubular member 140 by the wire securing mechanism 120.

In response to circulative movement of the wire 52, the main shaft 128 rotates in the yawing directions about the first rotational axis Oy to cause the support bar 144 to swing in an XZ plane.

The tubular member 140, the gear body 126, and the gear body 130 are stacked together along the shaft 112 and have a combined height which is essentially equal to the height H such that they are disposed with substantially no clearances between the tongues 58.

The drive mechanism 102 comprises a drive base 150, a gear ring 152, a geared pin 154, fastening nuts 156, 158, and a cover 160. The fastening nut 156 has a plurality of radial small holes 156a defined therein for inserting a narrow rotary tool. At least one of the small holes 156a is exposed radially (see FIG. 2) for allowing the fastening nut 156 to be turned without the need for the removal of the cover 160. The fastening nut 158 has parallel surfaces 158a engageable by a rotary tool such as a wrench or the like.

The drive base 150 includes a tubular member 164 rotatably fitted over a proximal portion of the support bar 144, a pair of support arms 166 projecting in the Z1 direction from respective opposite side portions of the tubular member 164, and a face gear 168 disposed on an end face of the tubular member 164 which faces the Z2 direction. The support arms 166 serve to support the end effector 104, and have respective holes 166a defined therein which are lined up with each other in the Z directions. After the tubular member 164 is fitted over the proximal portion of the support bar 144, the fastening nut 156 is threaded over the externally threaded distal end portion of the support bar 144, whereupon the drive base 150 is rotatably supported on the support bar 144 for rotation in the rolling directions about the axis of the support bar 144, i.e., about the second rotational axis Or.

The face gear 168 is held in mesh with the third gear 138. Consequently, the drive base 150 is rotatable about the second rotational axis Or in response to rotation of the tubular member 136.

The gear ring 152 is in the form of a thin tubular member including a face gear 170 on an end face thereof facing the Z2 direction and a face gear 172 on an end face thereof facing the Z1 direction. The gear ring 152 is fitted over the tubular member 164 of the drive base 150 for sliding rotation with respect to the outer circumferential surface of the tubular member 164. The gear ring 152 is fitted over the tubular member 164 such that the face gear 170 is slightly displaced off the face gear 168 of the drive base 150 in the Z1 direction and is held in mesh with the second gear 134. Since the face gear 170 is in mesh with the second gear 134, the gear ring 152 is rotatable about the second rotational axis Or in response to rotation of the gear body 126.

The geared pin 154 includes a fourth gear (joint driven gear) 174 held in mesh with the face gear 172 and a pin 176 extending in the X1 direction from the center of the fourth gear 174. The pin 176 has an externally threaded distal end portion. The pin 176 extends through the two holes 166a in the support arms 166 and has its externally threaded distal end portion projecting from one of the support arms 166 which is positioned remotely from the fourth gear 174. The fastening nut 158 is threaded over the projecting externally threaded distal end portion of the pin 176. The geared pin 154, with the fourth gear 174 held in mesh with the face gear 172, is rotatably supported by the support arms 166. The pin 176 has a D-shaped cross section for engagement with a portion of the end effector 104.

The cover 160 serves to protect the components of the drive mechanism 102, and covers the gear ring 152 and the fourth gear 174 against radial exposure. The cover 160 includes a short tube 180 extending in the Z2 direction and a pair of ears 182 projecting in the Z1 direction from respective opposite side portions of the short tube 180. The ears 182 are of such a shape that circumferential wall portions of the short tube 180 extend in the Z1 direction at the same diameter smoothly into the respective ears 182. The cover 160 has a lower portion fastened to a portion of the end effector 104 by a cover fastening pin 162. The cover 160 has a diameter which is equal to or smaller than the connector 16 as viewed in front elevation.

With such a drive mechanism 102, when the gear body 130 rotates, its rotation is transmitted from the third gear 138 to the face gear 168, rotating the drive base 150 and the end effector 104 connected thereto about the second rotational axis Or. When the gear body 114 rotates, its rotation is transmitted from the first gear 118 to the pin 176 through the second gear 134, the face gear 170, the face gear 172, and the fourth gear 174, rotating the geared pin 154.

The cover 160 may be in the form of a hollow cylindrical or conical cover for covering the drive mechanism 102 and the end effector 104 almost in their entirety to the extent that the operation of the drive mechanism 102 and the end effector 104 will not be hampered. The cover 160 may be fastened to the end effector 104 by a pin 196.

The end effector 104 comprises a first end effector member 190, a second end effector member 192, a link 194, and a pin 196. The pin 196 is axially aligned with the third rotational axis Og.

The first end effector member 190 includes a pair of laterally spaced side walls 200 facing each other and having respective holes 200a defined in front end portions thereof and respective holes 200b defined in rear end portions thereof, a first gripper 202 projecting in the Z1 direction from lower front end portions of the side walls 200, and a cover mount 204 disposed on rear lower end portions of the side walls 200. The holes 200a are of such a diameter that the pin 196 can be press-fitted therein. The first gripper 202 is slightly tapered along the Z1 direction and has an arcuate distal end portion. The first gripper 202 has a number of closely spaced teeth on an entire surface thereof which faces the Y1 direction.

The front end portions of the side walls 200 are arcuate in shape. The rear end portions of the side walls 200 have respective recesses 200c defined in outer surfaces thereof for receiving the respective support arms 166 of the drive mechanism 102. The first end effector member 190 has a hole 190a (see FIG. 5) defined between the first gripper 202 and the cover mount 204 for preventing interference with the rear end portion of the second end effector member 192. The cover mount 204 has a hole defined therein for passage of the cover fastening pin 162 therethrough.

The second end effector member 192 comprises a base 210, a second gripper (first working unit) 212 projecting in the Z1 direction from a front end of the base 210, a pair of ears 214 extending in the Z2 direction from laterally spaced rear end portions of the base 210, and a shaft support sleeve 216 disposed on a lower surface of the front end of the base 210. The shaft support sleeve 216 has a hole 216a defined therein which has an inside diameter large enough to receive the pin 196 inserted therein. When the pin 196 is inserted into the shaft support sleeve 216 and press-fitted in the hole 200a, the second end effector member 192 is made swingable about the third rotational axis Og. The second gripper 212 is identical in shape to the first gripper 202, but is in an upside-down orientation with respect to the first gripper 202. When the second end effector member 192 is turned counterclockwise in FIG. 4 about the third rotational axis Og, the second gripper 212 is brought into abutment against the first gripper 202, gripping a curved needle 930 (see FIG. 22A) or the like therebetween. The ears 214 have oblong holes 214a defined respectively therein.

The link 194 has a hole 220 defined in an end thereof and a pair of engaging fingers 222 disposed on the other end therefore and projecting laterally away from each other. The engaging fingers 222 slidably engage in the respective oblong holes 214a. The hole 220 is of a D-shaped cross section for receiving the pin 176 snugly therein. Therefore, the hole 220 serves to position the pin 176 and prevent the pin 176 from rotating about its own axis. When the pin 176 is inserted in the holes 166a and the holes 200b, 220 and the fastening nut 158 is threaded over the projecting externally threaded distal end portion of the pin 176, the link 194 is made swingable about the pin 176.

Figure 7A:
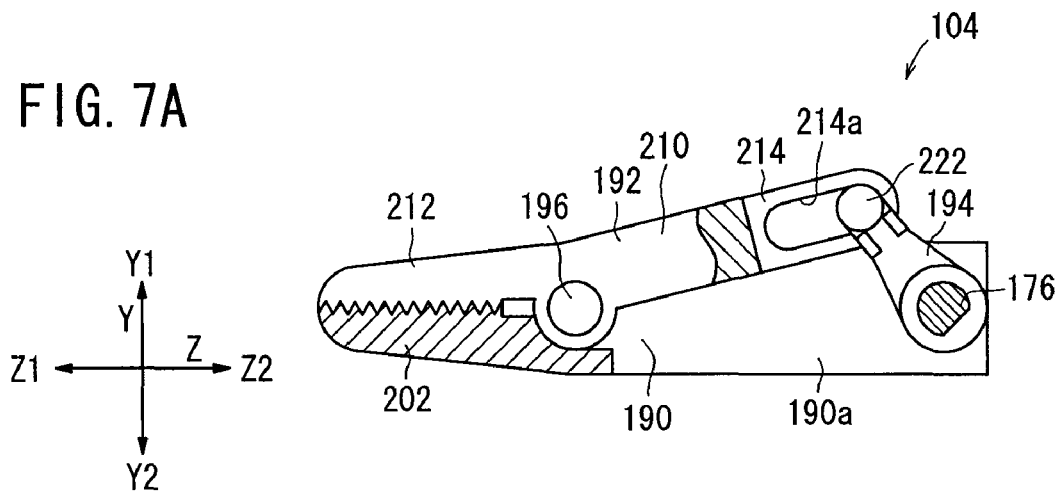
FIG. 7A is a side elevational view, partly in cross section, of an end effector with a gripper being closed.
Figure 7B:
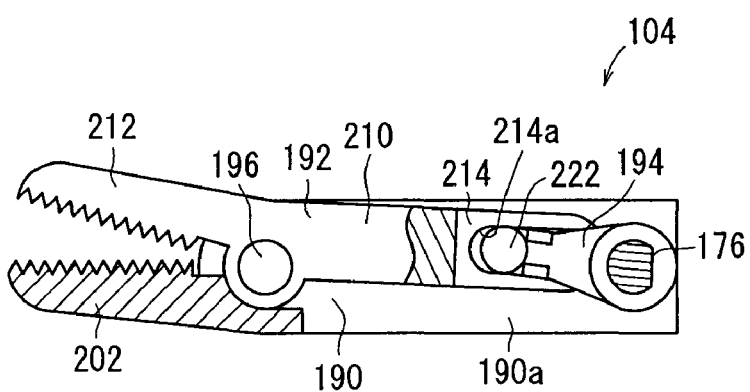
FIG. 7B is a side elevational view, partly in cross section, of the end effector with the gripper being slightly open.
Figure 7C:
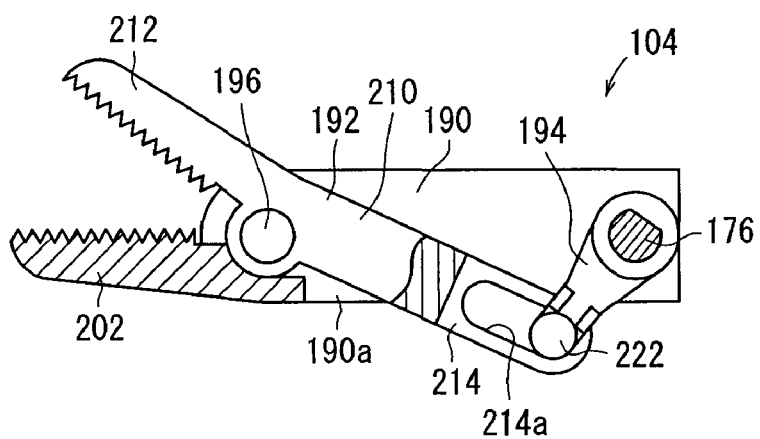
FIG. 7C is a side elevational view, partly in cross section, of the end effector with the gripper being fully open.

As shown in FIGS. 7A through 7C, the end effector 104 operates as follows: When the geared pin 154 rotates, the link 194 swings to cause the engaging fingers 222 to lift or lower the rear end portion of the second end effector member 192 in one of the Y directions while the engaging fingers 222 is being guided by the oblong holes 214a. Since the second end effector member 192 is swingable about the third rotational axis Og, the second end effector member 192 swings in response to the swinging movement of the link 194, closing the second gripper 212 toward the first gripper 202 or opening the second gripper 212 away from the first gripper 202. The end effector 104 with the link 194 functions as a torque mechanism for amplifying gripping forces of the first and second grippers 202, 212.

When the second gripper 212 is moved away from the first gripper 202, the ears 214 which are positioned remotely from the second gripper 212 are displaced in the Y2 direction. Since the first end effector member 190 has the hole 190a, the first end effector member 190 and the second end effector member 192 will not interfere with each other.

Figure 8:
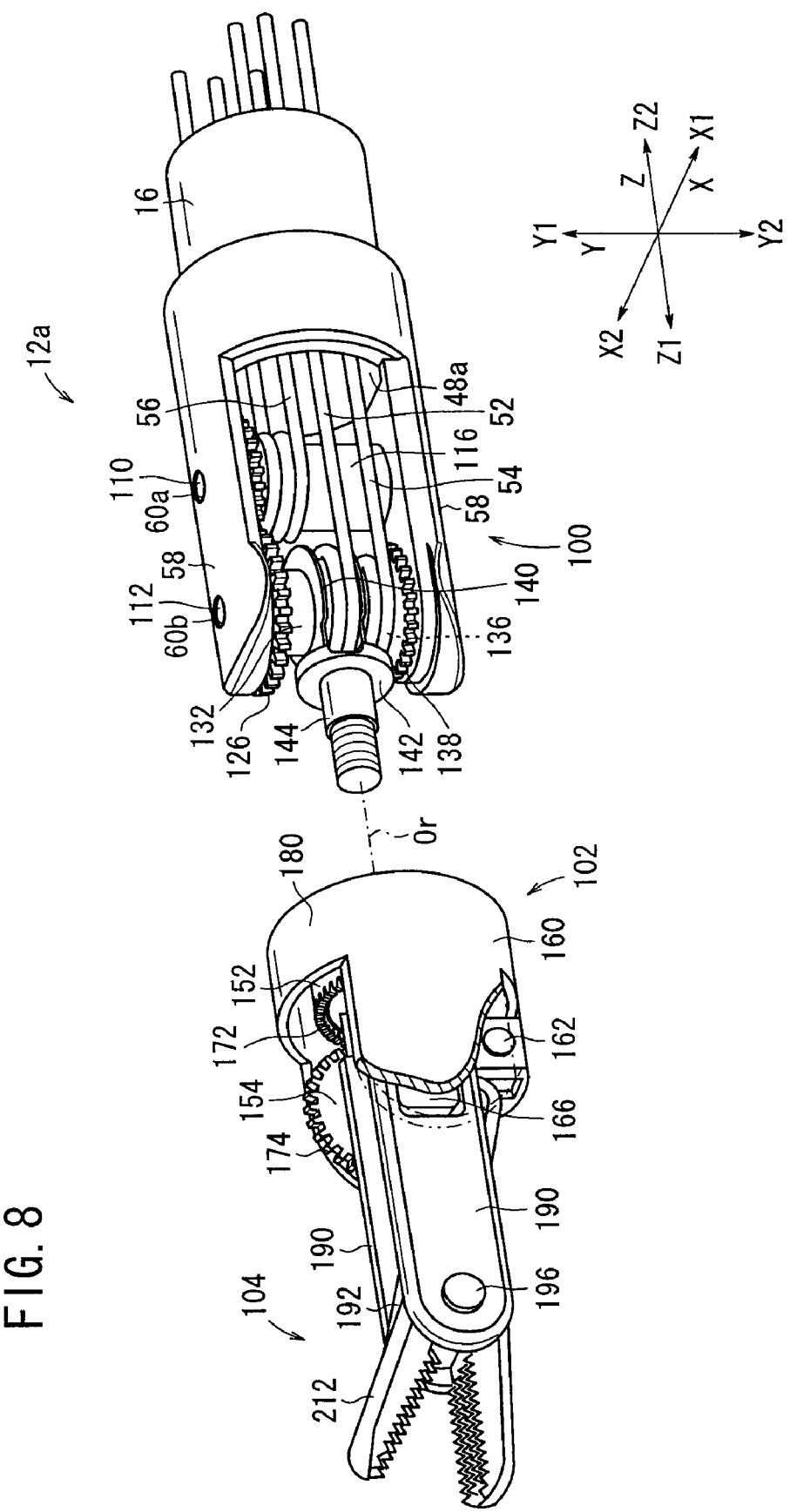
FIG. 8 is an exploded perspective view of the working unit according to the first embodiment.

As shown in FIG. 8, the working unit 12a can be disassembled into the wire-driven mechanism 100 and the other components, i.e., the drive mechanism 102 and the end effector 104. Therefore, the drive mechanism 102 and the end effector 104 can be replaced with other mechanisms when necessary.

Figure 5:
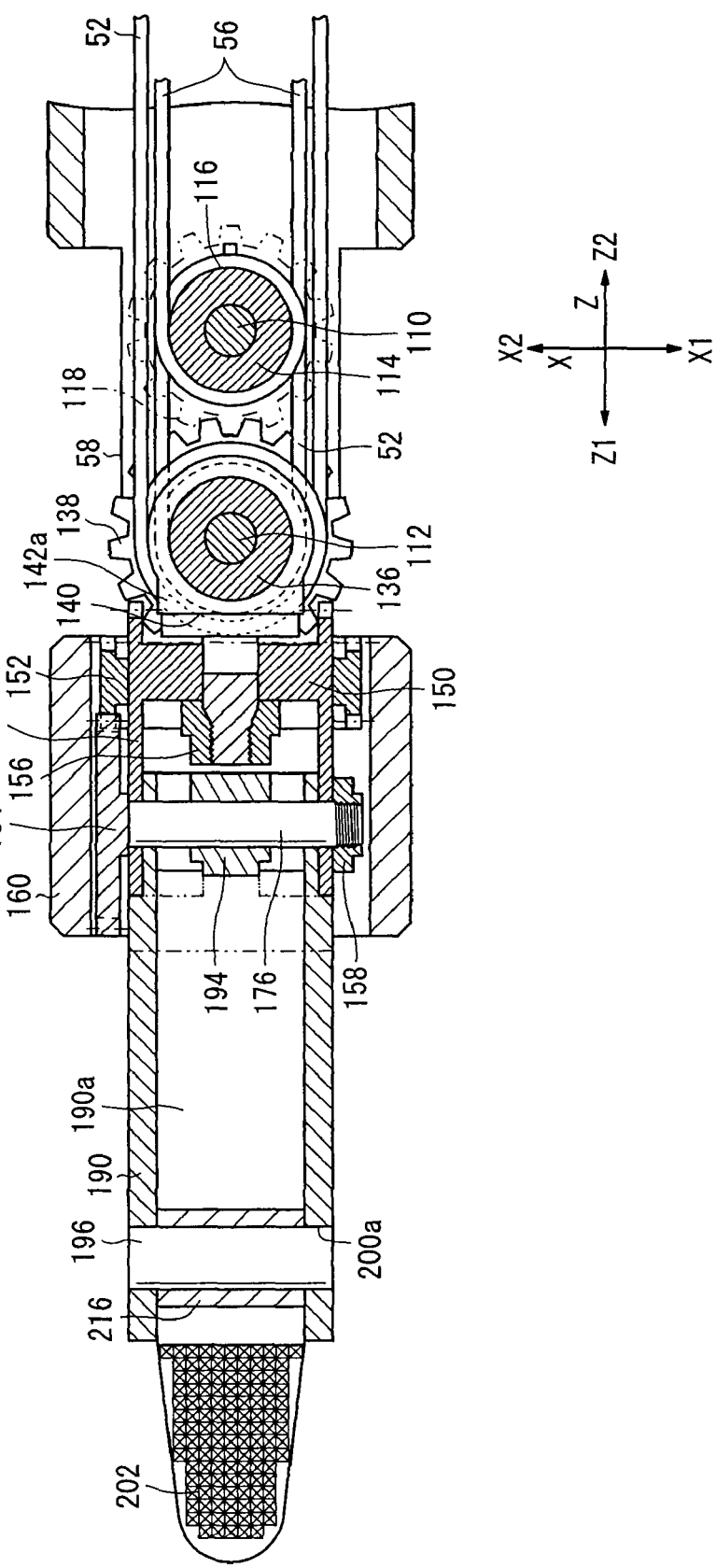
FIG. 5 is a sectional plan view of the working unit according to the first embodiment.

The wire 52 is wound for 1.5 turns around the tubular member 140, the wire 54 is wound for 1.5 turns around the tubular member 136, and the wire 56 is wound for 2.5 turns (900°) around the tubular member 116. As shown in FIG. 5, the tubular member 140 has a diameter set to a value equal to or greater than the sum of the diameter of the tubular member 116 and the diameters of two wires 56. As viewed in plan, the wires 52, 54 are disposed slightly outwardly of the wire 56. The wires 52, 54, 56 are therefore kept out of interference with each other.

Specifically, since the wire 56 is disposed inwardly of the wire 52, the wire 56 is kept out of interference with the wire 52. The wire 56 can be wound around the tubular member 116 over a region 116a thereof (see FIG. 4) which is about two-thirds of the overall height (H–D1) of the tubular member 116. The region 116a is wide enough to allow the wire 56 to be wound for 2.5 turns or more (e.g., 3.5 turns (1260°)) therearound, so that the gear body 114 can be rotated to make 2.5 revolutions or more. Since the angular displacement of the gear body 114 is large, the gear ratio between the first gear 118 and the second gear 134 can be increased to increase the rotational torque of the gear body 126.

If the gear body 114 and the first gear 118 are dispensed with and the wire 56 is wound around the tubular member 132 to directly rotate the gear body 126, then a region 132a (see FIG. 4) around which the wire 56 is wound is limited by the height of the tubular member 132, and is much smaller than the region 116a (about two-thirds of the overall height) or about one-half the region 116a. The wire 56 can thus be wound around the region 132a which is represented by the remainder produced after the heights of the tubular member 140 and the tubular member 136 are subtracted from the height H, and is wound about 1.5 turns (540°) around the region 132a, as with the wire 54 wound around the tubular member 136. As a result, the angular displacement of the gear body 126 and the rotational torque thereof are small.

The working unit 12a of the manipulator 10 according to the first embodiment, however, includes the gear body 126 which is disposed in front of the tubular member 116 with the wire 56 wound therearound and whose rotational shaft is substantially parallel to the tubular member 116, and the first gear 118 and the second gear 134 for transmitting the rotation of the gear body 114 to the gear body 126. The number of turns of the wire 52, the size of the main shaft 128, and the size of the gear body 130, which are positioned forwardly of the tubular member 116, have no adverse effect on the manner in which the wire 56 is wound around the tubular member 116. Accordingly, the wire 56 can wound around the tubular member 116 over the region 116a which is about two-thirds of the overall height of the tubular member 116. The angular displacement of the gear body 114 can thus be increased, resulting in an increase in the angular displacement and the rotational torque of the gear body 126 that is driven by the gear body 114 for operating the second gripper 212 reliably through a large angular range. Since the angular displacement and the rotational torque of the gear body 126 are large, the drive forces applied to the second gripper 212 by the gear body 126 are also large to cause the second gripper 212 to be pressed strongly against the first gripper 202 for reliably holding the curved needle 930 (see FIG. 22A), for example.

If the diameter of the tubular member 136 and the diameter of the tubular member 140 are equal to each other, then the wire 56 can be wound around the tubular member 116 almost fully over the region 116a irrespectively of the positions of the wires 52, 54. Accordingly, the angular displacement and the rotational torque of the gear body 126 can further be increased.

Operation of the manipulator 10a thus constructed will be described below with reference to FIG. 9.

First, the manipulator 10a is actuated in a yawing direction by operating the first instruction lever 34 (see FIG. 1) with a finger. Specifically, when the surgeon who handles the manipulator 10a operates the first instruction lever 34 with a finger, the motor 40 (see FIG. 1) is energized to rotate the drive pulley 50a to circulatively move the wire 52, rotating the main shaft 128 about the first rotational axis Oy. The drive mechanism 102 (second acting unit) and the end effector 104 (second acting unit) that are connected to the support bar 144 of the main shaft 128 are now caused to swing in the yawing direction.

The first instruction lever 34 is tiltable selectively in normal and reverse directions. When the first instruction lever 34 is tilted in a direction, the end effector 104 is actuated in a corresponding one of the yawing directions, i.e., in a normal direction or a reverse direction. When the surgeon returns the first instruction lever 34 to its neutral position, the motor 40 is de-energized, holding the end effector 104 in the position reached in the yawing direction at the moment. Alternatively, the end effector 104 may be instructed to swing through an angle in a yawing direction which is proportional to the angle through which the first instruction lever 34 is angularly moved. The end effector 104 may be instructed to move at a certain speed or to move to a certain position (or through a certain angle).

The manipulator 10a is actuated in a rolling direction by operating the second instruction lever 36 (see FIG. 1) with a finger. Specifically, when the surgeon operates the second instruction lever 36 with a finger, the motor 42 (see FIG. 1) is energized to rotate the drive pulley 50b to circulatively move the wire 54, rotating the gear body 130, whose rotation is transmitted through the third gear 138 and the face gear 168 to the drive base 150. The drive base 150 is now rotated about the second rotational axis Or. The drive mechanism 102 and the end effector 104 are now caused to rotate in the rolling direction.

The second instruction lever 36 is tiltable selectively in normal and reverse directions. When the second instruction lever 36 is tilted in a direction, the end effector 104 is actuated in a corresponding one of the rolling directions, i.e., in a normal direction or a reverse direction. When the surgeon returns the second instruction lever 36 to its neutral position, the motor 42 is de-energized, holding the end effector 104 in the position reached in the rolling direction at the moment. Alternatively, the end effector 104 may be instructed to turn through an angle in a rolling direction which is proportional to the angle through which the second instruction lever 36 is angularly moved. The end effector 104 may be instructed to move at a certain speed or to move to a certain position (or through a certain angle).

The end effector 104 is selectively opened and closed by pulling the trigger lever 32 (see FIG. 1) with a finger. Specifically, when the surgeon pulls the trigger lever 32 with a finger, the motor 44 (see FIG. 1) is energized to rotate the drive pulley 50c to circulatively move the wire 56, rotating the gear body 114, whose rotation is transmitted through the first gear 118, the second gear 134, the face gears 170, 172, and the fourth gear 174 to the pin 176. The pin 176 causes the link 194 to turn the second end effector member 192 about the third rotational axis Og. The second gripper 212 (first acting unit) is now opened away from or closed toward the first gripper 202.

The trigger lever 32 can be pulled by a finger, and return to its original position under resiliency when it is released from the finger. The end effector 104 operates in ganged relation to the trigger lever 32 such that the end effector 104 is closed when the trigger lever 32 is pulled and returns to its open position when the trigger lever 32 is released. The trigger lever 32 may be combined with a latch mechanism.

Figure 9:
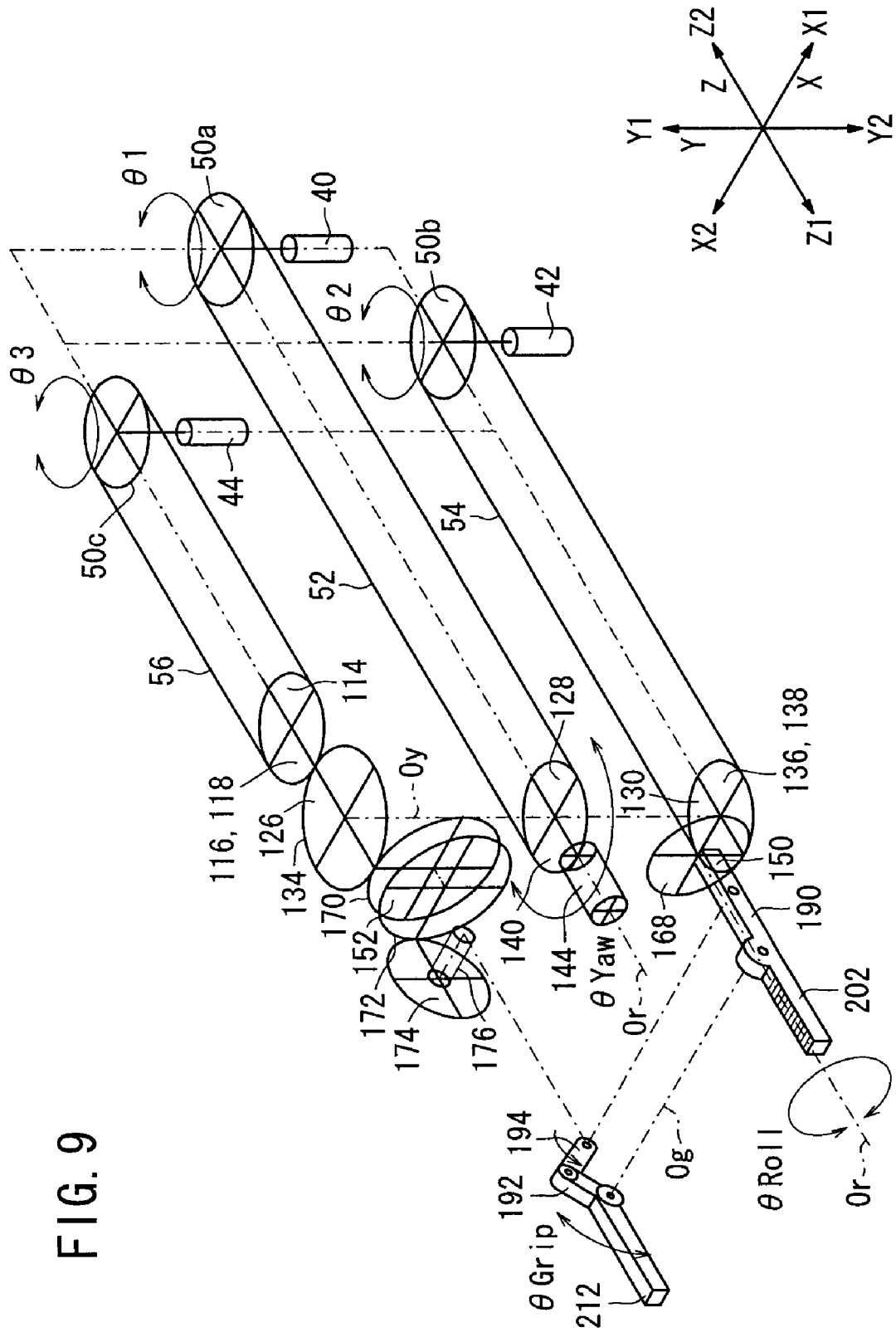
FIG. 9 is a schematic perspective view of an actuating system of the manipulator according to the first embodiment.

Drive-side rotational angles ($\theta_1$, $\theta_2$, $\theta_3$) and distal joint angles ($\theta_{Yaw}$, $\theta_{Roll}$, $\theta_{Grip}$) are defined as shown in FIG. 9. The drive-side rotational angles ($\theta_1$, $\theta_2$, $\theta_3$) and distal joint angles ($\theta_{Yaw}$, $\theta_{Roll}$, $\theta_{Grip}$) are expressed by the following equation (1):

$$\begin{bmatrix} \theta_1 \\ \theta_2 \\ \theta_3 \end{bmatrix} = \begin{bmatrix} 1 & 0 & 0 \\ 1 & -1 & 0 \\ -1 & -1 & \alpha \end{bmatrix} \begin{bmatrix} \theta_{Yaw} \\ \theta_{Roll} \\ \theta_{Grip} \end{bmatrix} \quad (1)$$

For brevity, the drive mechanisms involving the angles $\theta_1$ through $\theta_{Yaw}$ and the angles $\theta_2$ through $\theta_{Roll}$ have a speed reduction ratio of 1, and the drive mechanism involving the angles $\theta_3$ through $\theta_{Grip}$ has a speed reduction ratio $\alpha$. The speed reduction ratio $\alpha$ is a function determined by the ratio of the numbers of teeth of the first gear 118 and the second gear 134, the ratio of the first end effector member 190, the second end effector member 192, and the link 194, and the pulley diameters, etc. The relationship between the angles $\theta_3$, $\theta_{Grip}$ is expressed by the following equation (2):

$$\theta_3 = -\theta_{Yaw} - \theta_{Roll} + \alpha \theta_{Grip} \quad (2)$$

Therefore, depending on the angles $\theta_{Yaw}$, $\theta_{Roll}$, the angle $\theta_3$ needs to be large in order to open and close the second gripper 212 with respect to the first gripper 202. If $\theta_{Yaw} = -90°$ and $\theta_{Roll} = -180°$, then $\theta_{Grip} > 270°$. If $\theta_{Yaw} = +90°$ and $\theta_{Roll} = +180°$, then $\theta_{Grip} < -270°$. It can be understood that in order to open and close the second gripper 212, an operating range of ±270°, i.e., 540° (1.5 revolutions) is required. In other words, an operating range of $-270° - \alpha \cdot \theta_{Grip\text{-}min} \leq \theta_3 \leq 270° + \alpha \cdot \theta_{Grip\text{-}max}$.

As described above, the working unit 12a mounted on the distal end of the manipulator 10a according to the first embodiment includes, forwardly of the tubular member 116 around which the wire 56 is wound, the gear body 126 whose rotational axis extends substantially parallel to the tubular member 116, and the first gear 118 and the second gear 134 for transmitting the rotation of the gear body 114 to the gear body 126. Since the tubular member 116 is offset from the gear body 126, the number of turns of the wire 52 and the sizes of the main shaft 128 and the gear body 130, which are located forwardly of the tubular member 116, do not adversely affect the turns of the wire 56 around the tubular member 116, allowing the wire 56 to be wound around the region 116a which is about two-thirds of the overall height of the tubular member 116, so that the gear body 114 can rotate through a large angle. Therefore, the angular displacement and rotational torque of the gear body 126 can be increased. As a result, the second gripper 212 can largely and reliably be operated with respect to the first gripper 202 for increased operability. The manipulator 10a and the working unit 12a are simple in structure and highly reliable.

As shown in FIG. 5, the diameter of the tubular member 140 is set to a value equal to or greater than the sum of the diameter of the tubular member 116 and the diameters of two wires 56. The wire 52 is thus disposed slightly outwardly of the wire 56, so that they are kept out of interference with each other, allowing the wire 56 to be wound reliably around the tubular member 116.

The winding angle through which the wire 56 is wound around the tubular member 116 is increased for higher reliability of the wire and pulley drive system. Specifically, according to torque transmission based on the friction between a pulley and a wire wound therearound, the greater the winding angle of the wire is, the greater torque can be transmitted if the initial tension of the wire remains the same. The wire 56 can transmit a greater torque to the tubular member 116 under frictional forces even in the absence of a securing means such as the wire securing mechanism 120. If the wire securing mechanism 120 is dispensed with, then the wire 56 is free of a local excessive load which would otherwise be applied by the fastening pin 124. Therefore, the wire 56 can have a longer service life and increased reliability, and the angular displacement and rotational torque of the gear body 126 can be increased.

The working unit 12a provides a yaw-axis operating range of ±90°, a roll-axis operating range of ±180°, and a gripper opening/closing angle of about 40° (which may change depending on the linkage ratio). An increase in the roll-axis operating range makes it possible to guide the curved needle 930 with ease for better operability.

The working unit 12a is a simple structure compared with the working unit 900 (see FIG. 21) because the working unit 12a is basically provided by adding the gear body 114 to the working unit 900. Since the working unit 12a can be small in size and light in weight, it can suitably be used to operate in small body regions. Particularly, since the added bear body 114 is disposed parallel to the gear body 126 in the Z directions, the working unit 12a is prevented from having increased widths in the X and Y directions.

Since the working unit 12a can be small in diameter as with the working unit 900, the trocar 20 (see FIG. 1) that is placed in an abdominal or chest part of the patient in combination with the working unit 12a can also be small in size and diameter. Accordingly, the working unit 12a is minimally invasive to the patient.

The power of the gear body 114 is transmitted simply and reliably to the gear body 126 through the first gear 118 and the second gear 134 which serve as a gear pair.

The main shaft 128 and the gear bodies 126, 130 are disposed coaxially with each other, and share the shaft 112. Consequently, the main shaft 128 and the gear bodies 126, 130 are of a simple structure.

Compared with the working unit 900 shown in FIG. 21, the working unit 12a is improved in its reliability. In the working unit 900, all tension of the three wires 902, 903, 904 is concentrated on the support shaft 920. In contrast, in the working unit 12a, since tension of the wires is distributed to the shaft 110 and to the shaft 112, bending stress applied to each of the shafts 110, 112 is reduced. That is, because the tension of only the two wires 52, 54 acts on the shaft 112, and the tension of only the wire 56 acts on the shaft 110, bending stress applied to each of the shafts 112, 110 is reduced. In the embodiment shown in FIG. 19, which will be referred to later, since three shafts 110, 112, 500 are provided, bending stress applied to each shaft is further reduced.

Figure 10:
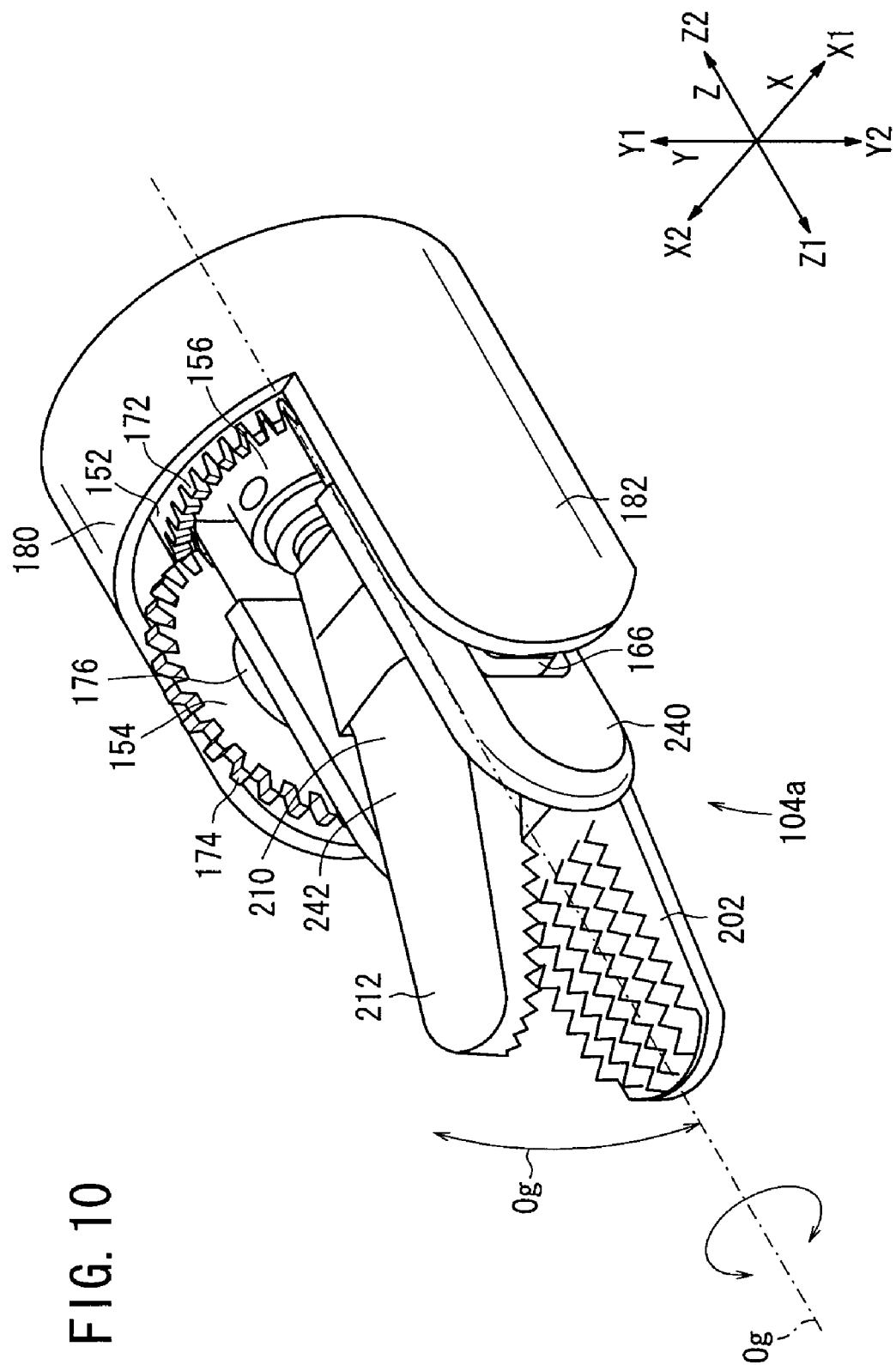
FIG. 10 is a perspective view of a modification of the working unit according to the first embodiment.
Figure 11:
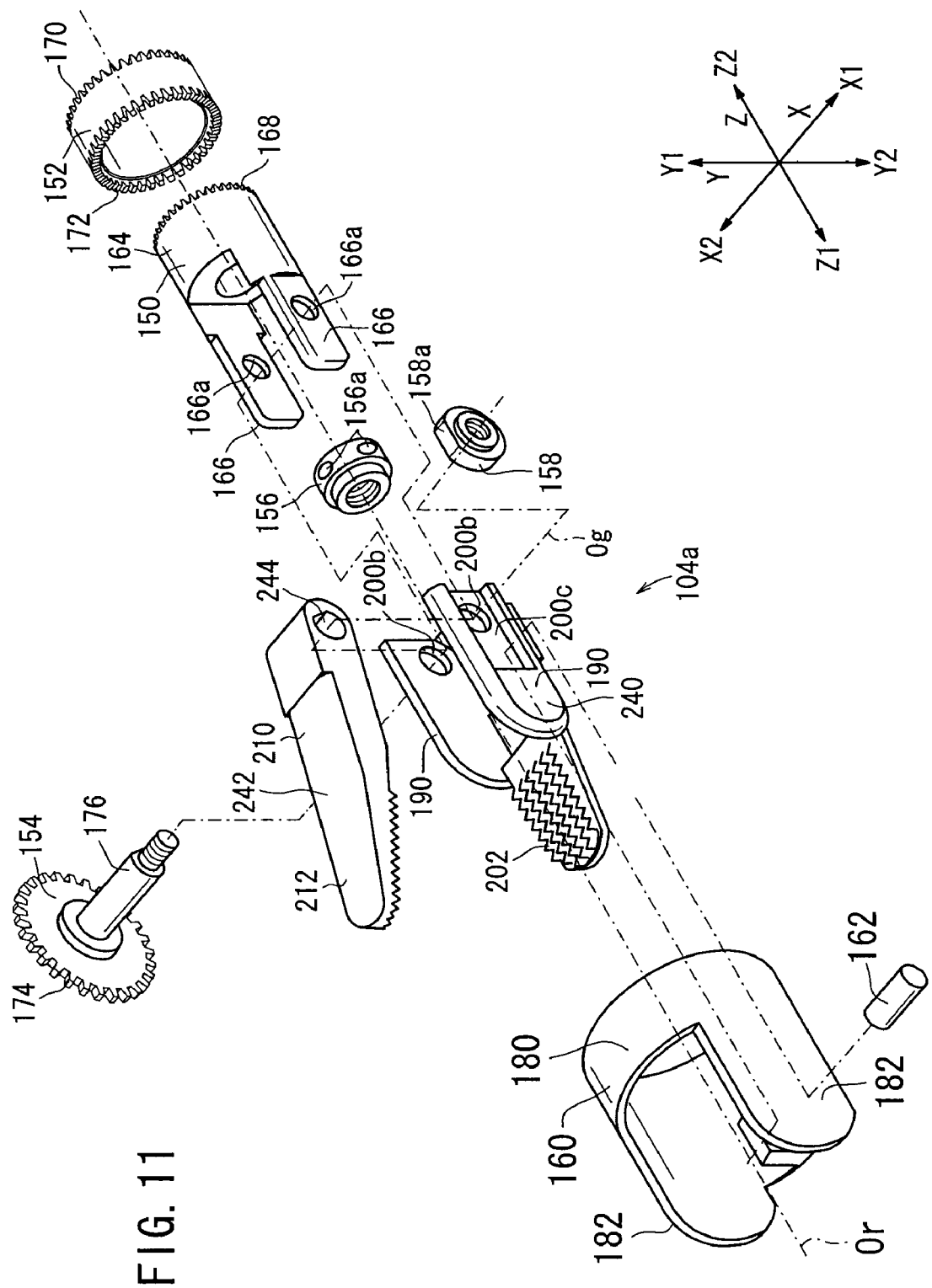
FIG. 11 is an exploded perspective view of the modification of the working unit according to the first embodiment.

The end effector 104 of the working unit 12a is not limited to the toggle mechanism employing the link 194, but may be an end effector 104a shown in FIGS. 10 and 11. Those parts of the end effector 104a and other end effectors to be described later which are identical to those of the manipulator 10a and the working unit 12a are denoted by identical reference characters, and will not be described in detail below.

The end effector 104a includes a first end effector member 240 and a second end effector member 242 which correspond respectively to the first end effector member 190 and the second end effector member 192. The end effector 104a is free of a member corresponding to the link 194.

The first end effector member 240 is free of the hole 190a of the first end effector member 190, and is shorter than the first end effector member 190 in the Z directions. The second end effector member 242 is free of the ears 214 and the shaft support sleeve 216 of the second end effector member 192, and has the base 210 shorter than the second end effector member 192. The base 210 has a hole 244 of a D-shaped cross section defined in the rear end thereof, which corresponds to the hole 220. The pin 176 is inserted in the hole 224, so that the second end effector member 242 can be directly actuated by the geared pin 154.

The end effector 104a is of a simple structure and can easily be assembled and serviced for maintenance.

A manipulator 10b according to a second embodiment of the present invention will be described below with reference to FIGS. 12 through 16. The manipulator 10b has an operation command unit 14 and a connector 16 which are identical to the operation command unit 14 and the connector 16 of the manipulator 10a, and includes a working unit 12b instead of the working unit 12a. The manipulator 10b functions as an electrosurgical knife for passing an electric current from the working unit 12b to a living tissue at a high frequency to coagulate, cut, or treat a desired area of the living tissue.

Figure 13:
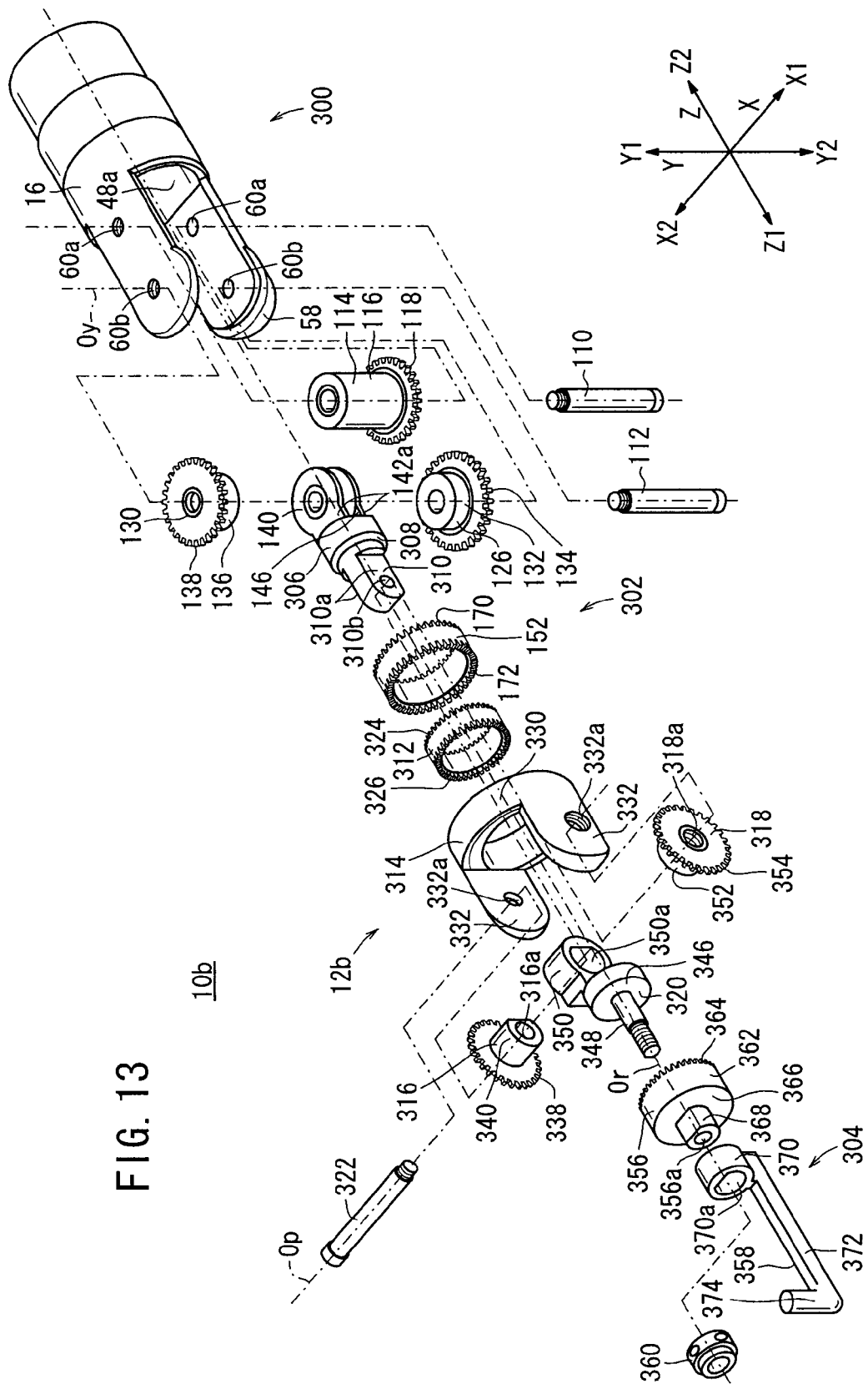
FIG. 13 is an exploded perspective view of the working unit according to the second embodiment.
Figure 14:
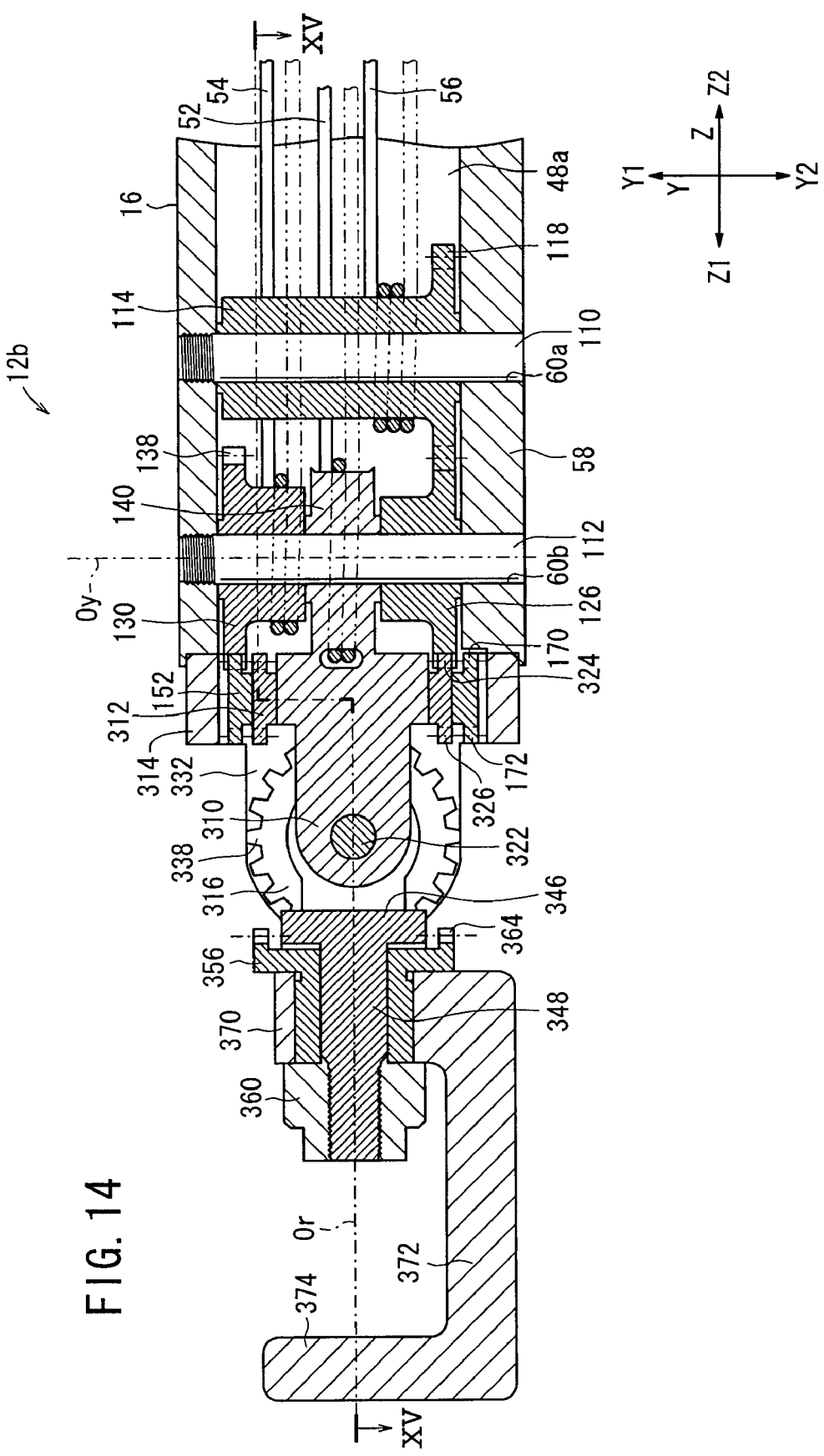
FIG. 14 is a sectional side elevational view of the working unit according to the second embodiment.
Figure 15:
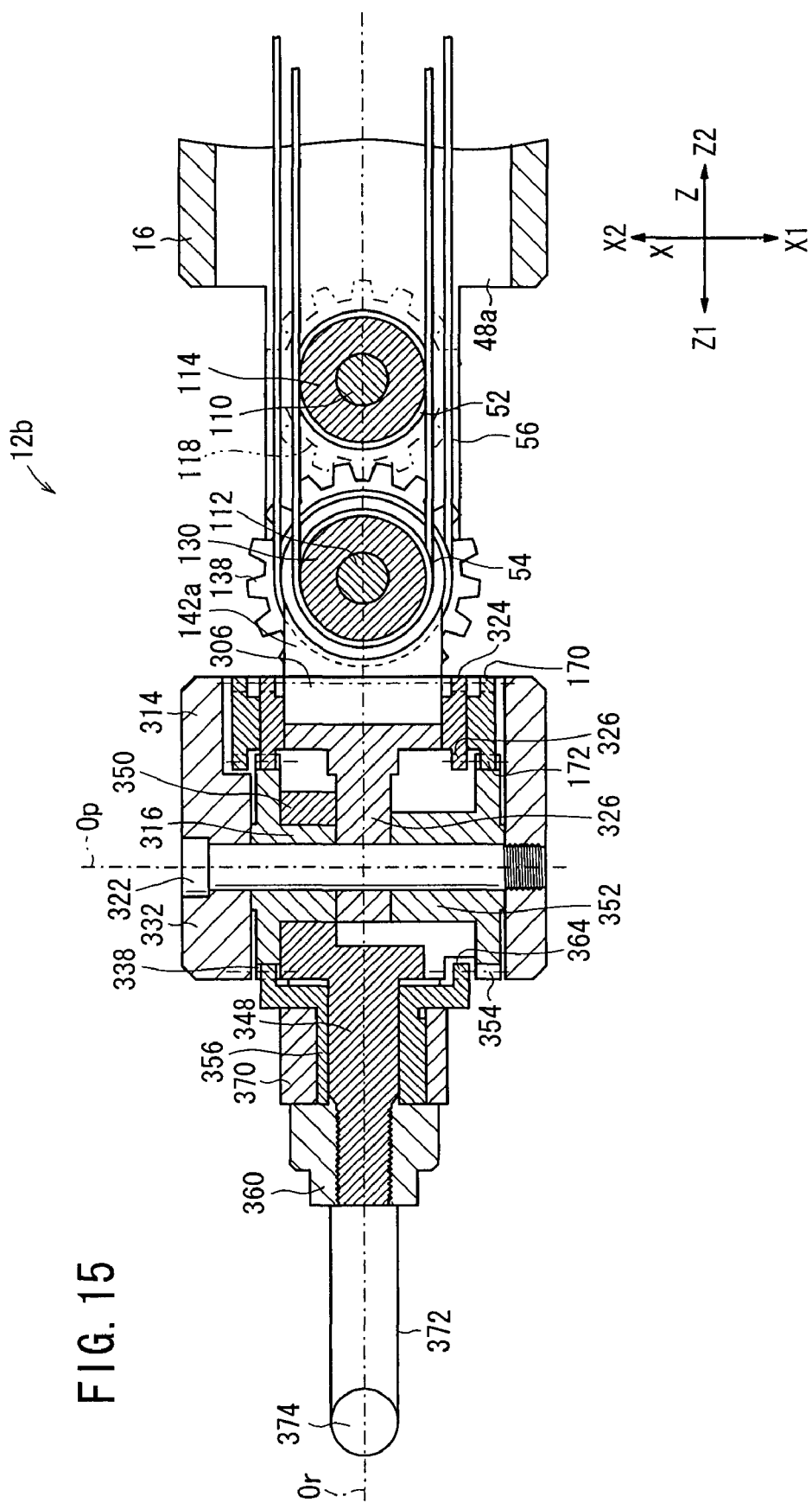
FIG. 15 is a sectional plan view of the working unit according to the second embodiment.

As shown in FIGS. 12 through 14, the working unit 12*b* incorporates therein mechanisms of three degrees of freedom. These mechanisms include a mechanism having a first degree of freedom for angularly moving a portion of the working unit 12*b* that is positioned ahead of a first rotational axis Oy extending along the Y directions, in yawing directions about the first rotational axis Oy, a mechanism having a second degree of freedom for angularly moving the portion of the working unit 12*b* in rolling directions about a second rotational axis Or extending along the Z directions, and a mechanism having a third degree of freedom for angularly moving an end effector 104 on the distal end of the working unit 12*b* in pitching directions about a third rotational axis Op. The working unit 12*b* comprises a wire-driven mechanism 300, a drive mechanism 302, and the end effector 304.

The wire-driven mechanism 300, the drive mechanism 302 and the end effector 304 will be described in detail referring to FIGS. 12 through 15.

The wire-driven mechanism 300 corresponds to the wire-driven mechanism 100 according to the first embodiment, but has gear bodies 114, 126, 130 disposed upside down about an axis with respect to the wire-driven mechanism 100. The wire-driven mechanism 300 includes shafts 110, 112 having respective externally threaded ends that are threaded and secured in the respective shaft holes 60*a*, 60*b* formed along the Y1 direction.

A main shaft 306 that is disposed between the gear bodies 126, 130 corresponds to the main shaft 128. The main shaft 306 comprises a slightly thick annular seat 308 and a pitch base 310 extending in the Z1 direction from the center of the annular seat 308. The pitch base 310 is a member serving as a basis for movement in the pitching directions, and includes a pair of laterally spaced parallel slide surfaces 310*a* for defining movement in the pitching directions and a hole 310*b* defined in a distal end thereof and extending between the slide surfaces 310*a*. The hole 310*b* serves as the center of rotation of the end effector 304.

As with the wire-driven mechanism 100, the wire-driven mechanism 300 includes tubular members 140, 136, 116 around which respective wires 52, 54, 56 are wound.

The wire-driven mechanism 300 enables the main shaft 306 to swing in the yawing directions about the first rotational axis Oy.

The drive mechanism 302 comprises gear rings 152, 312, a cover 314, gear bodies 316, 318, an end effector main shaft 320, and a securing pin 322.

The gear ring 312 is in the form of a thin tubular member including a face gear 324 on an end face thereof facing the Z2 direction and a face gear 326 on an end face thereof facing the Z1 direction. The gear ring 312 is fitted in the gear ring 152 for sliding rotation with respect to the inner circumferential surface of the gear ring 152. The face gear 324 is held in mesh with the second gear 134, so that the gear ring 312 is rotatable about the second rotational axis Or in response to rotation of the gear body 126.

The cover 314, which corresponds to the cover 160, serves to protect and support the components of the drive mechanism 302. The cover 314 includes a short tube 330 extending in the Z2 direction and a pair of ears 332 projecting in the Z1 direction from respective opposite side portions of the short tube 330. The ears 332 have respective holes 332*a* defined therein for inserting and securing the securing pin 322 therein. One of the holes 332*a* is a hole for inserting the securing pin 322 therethrough, and the other hole 322*a* is a hole for threading the securing pin 322 therein. The ears 332 have respective parallel surfaces confronting each other, and have such a width that the gear bodies 316, 318, an engaging member 350, and the pitch base 310 are slidably held by the ears 332. The short tube 330 has an inner circumferential surface whose diameter is slightly greater than the diameter of the outer circumferential surface of the gear ring 152, with a clearance left therebetween.

The gear body 316 is positioned in a region between the ears 332, which is displaced in the X2 direction, and includes a fourth gear 338 and a boss 340 coupled centrally to the fourth gear 338 in concentric alignment therewith and having a D-shaped cross section. The gear body 316 is oriented such that the fourth gear 338 faces the X2 direction. The fourth gear 338 is held in mesh with the face gear 326. The gear body 316 has a central hole 316*a* defined therein through which the securing pin 322 is inserted.

The end effector main shaft 320 comprises a base disk 346, a main shaft 348 projecting in the Z1 direction from the base disk 346, and an engaging member 350 projecting in the Z2 direction from a surface of the base disk 346 which faces the Z2 direction at a position that is slightly displaced in the X2 direction from the center of the base disk 346.

The engaging member 350 has a hole 350*a* of a D-shaped cross section in which the boss 340 engages. The main shaft 348 has an externally threaded distal end portion. When the boss 340 is inserted into the hole 350*a*, the end effector main shaft 320 is integrally and stably combined with the gear body 316.

The gear body 318 is positioned in a region between the ears 332, is displaced in the X1 direction, and includes a tubular member 352 and a fifth gear 354 coupled to an end surface of the tubular member 352 in concentric alignment therewith. The gear body 318 is oriented such that the fifth gear 354 faces the X1 direction. The fifth gear 354 is held in mesh with the face gear 326. The gear body 318 has a central hole 318*a* defined therein through which the securing pin 322 is inserted.

The assembly of the gear body 318, the pitch base 310, the end effector main shaft 320, and the gear body 316 is disposed with substantially no clearances between the ears 332. The securing pin 322 is inserted through the holes 316*a*, 310*b*, 318*a* and supported therein. The assembly of the end effector main shaft 320 and the gear body 316 is swingable about the third rotational axis Op in response to rotation of the gear ring 152. The gear body 318 is rotatable in response to rotation of the gear ring 312.

In the drive mechanism 302 thus constructed, the rotation of the gear body 130 and the third gear 138 is transmitted through the gear ring 152 and the fourth gear 338 to the main shaft 348, which is angularly lifted or lowered about the third rotational axis Op. The rotation of the gear body 114 and the first gear 118 is transmitted through the second gear 134 and the gear ring 312 to the gear body 318 and the fifth gear 354.

The end effector 304 comprises a crown 356, an electrode unit 358, and a fastening nut 360.

The crown 356 includes a thin tubular member 362, a face gear 364 disposed on a surface of the tubular member 362 which faces the Z2 direction, a disk 366 closing the end of the tubular member 362 which faces the Z1 direction, and a boss 368 projecting in the Z1 direction from the center of the disk 366 and having a D-shaped cross section. The disk 366 and the boss 368 have a hole 356*a* defined therein for inserting the main shaft 348 therein.

The electrode unit 358 comprises a coupling 370 connected to the drive mechanism 302, an arm 372 extending in the Z1 direction from the coupling 370 at a position slightly offset from the second rotational axis Or, and an electrode 374 bent from the distal end of the arm 372 in the Y1 direction. The coupling 370 has a hole 370*a* of a D-shaped cross section into which the boss 368 is inserted. The illustrated electrode unit 358 has its distal end hook-shaped. However, the distal end may have a blade-shaped depending on a living tissue to be manipulated.

The fastening nut 360 is identical in shape to the fastening nut 158 according to the first embodiment. When the main shaft 348 of the drive mechanism 302 is inserted into the hole 356a in the crown 356 with the boss 368 inserted in the hole 370a, the externally threaded distal end portion of the main shaft 348 projects from the coupling 370 of the electrode unit 358. The fastening nut 360 is threaded over the projecting externally threaded distal end portion of the main shaft 348, thereby combining the end effector 304 with the drive mechanism 302. The crown 356 and the electrode unit 358 are now supported for angular movement around the main shaft 348. The face gear 364 is held in mesh with the fifth gear 354.

In such an end effector 304, when the gear body 318 and the fifth gear 354 are rotated, the crown 356 and the electrode unit 358 are rotated about the second rotational axis Or.

Figure 16:
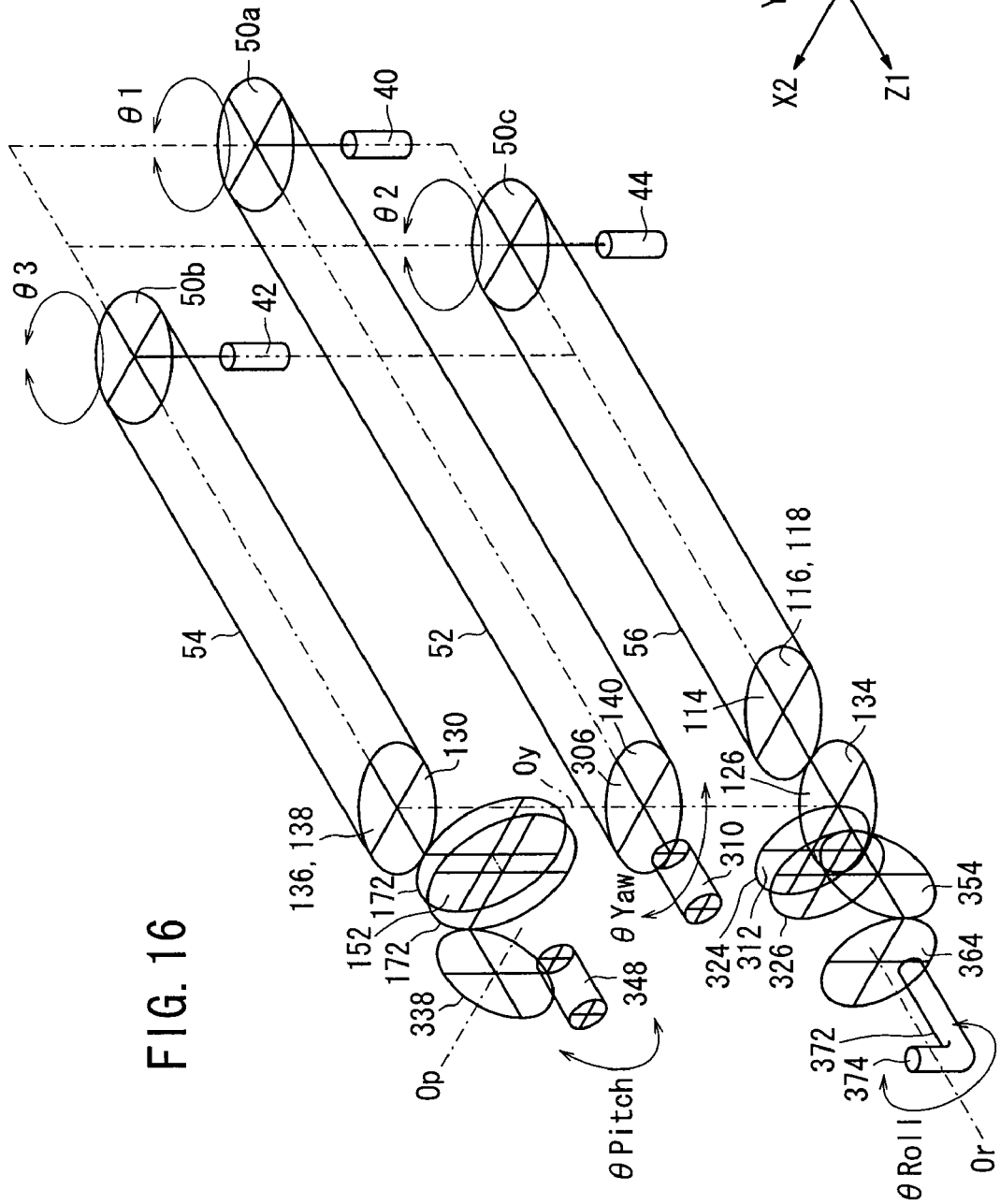
FIG. 16 is a schematic perspective view of an actuating system of a manipulator according to the second embodiment.

Operation of the manipulator 10b thus constructed will be described below with reference to FIG. 16.

The manipulator 10b is actuated in a pitching direction by operating the second instruction lever 36 (see FIG. 1) with a finger. Specifically, when the surgeon operates the second instruction lever 36 with a finger, the motor 42 (see FIG. 1) is energized to rotate the drive pulley 50b to circulatively move the wire 54, rotating the gear body 130, whose rotation is transmitted through the third gear 138 and the face gears 170, 172 and the fourth gear 338 to the gear body 316. The gear body 316 is now rotated in unison with the main shaft 348 about the third rotational axis Op.

The end effector 304 is rotated in a normal or reverse pitching direction depending on the direction in which the second instruction lever 36 is tilted. When the surgeon returns the second instruction lever 36 to its neutral position, the motor 42 is de-energized, holding the end effector 304 in the position reached in the pitching direction at the moment. The end effector 304 may be instructed to turn in a pitching direction based on a positioning command.

The manipulator 10b is actuated in a rolling direction by pulling the trigger lever 32 (see FIG. 1) with a finger. Specifically, when the surgeon pulls the trigger lever 32 with a finger, the motor 44 (see FIG. 1) is energized to rotate the drive pulley 50c to circulatively move the wire 56, rotating the gear body 114, whose rotation is transmitted through the first gear 118, the second gear 134, the face gears 324, 326, the fifth gear 354, and the face gear 364 to the end effector 304. The end effector 304 is now rotated about the second rotational axis Or.

The end effector 304 operates in ganged relation to the trigger lever 32 such that the end effector 304 is closed when the trigger lever 32 is pulled and returns to its open position when the trigger lever 32 is released. For operating the manipulator 10b in pitching directions, the manipulator 10b may employ input means tiltable in normal and reverse directions, such as the first instruction lever 34 and the second instruction lever 36, so that the end effector 304 keeps its angularly moved position at the time the input means is released from the finger. The trigger lever may be dispensed with, and a third instruction lever may be employed instead. Alternatively, the trigger lever may be used to change how the first instruction lever and the second instruction lever work.

The manipulator 10b operates in yawing directions in the same manner as with the manipulator 10a. Therefore, the operation of the manipulator 10b in yawing directions will not be described in detail below.

As indicated by the imaginary lines in FIG. 1, a power supply 380 applies a voltage between the connector 16 and the body region being treated, supplying an electric current from the tip end of the electrode 374 to the body region. The manipulator 10b thus serves as a monopolar electrosurgical knife.

With the working unit 12b of the manipulator 10b, as with the working unit 12a of the manipulator 10a, the number of turns of the wire 52, the size of the main shaft 128, and the size of the gear body 130, which are positioned forwardly of the tubular member 116, have no adverse effect on the manner in which the wire 56 is wound around the tubular member 116. Accordingly, the wire 56 can wound around the tubular member 116 over the region which is about two-thirds of the overall height of the tubular member 116. The angular displacement of the gear body 114 can thus be increased, allowing the number of turns of the wire 56 to be increased to increase the angular displacement of the gear body 114. Therefore, the angular displacement and the rotational torque of the gear body 126 are increased. The end effector 304 can be angularly moved for a large angular displacement in rolling directions about the second rotational axis Or, and can reliably be operated.

For the same reasons as given for the working unit 12a, in order to operating the drive shaft at the foremost end, particularly the end effector 304 through ±180° in the rolling directions (θRoll), the working unit 12b requires an operating range of θ2 taking into account the yaw operating range (θYaw)±90° and the pitch operating range (θPitch)±90°. The 1.5 turns of the wires are not sufficient, but the wires need to be wound through at least ±360°, i.e., in 2 turns. Since the wires are wound in a range of 2.5 to 3.5 turns in the working unit 12b, the working unit 12b provides an operating range of ±180° or more in the rolling directions (θRoll). Accordingly, the operating range in the rolling directions is increased, and the end effector 304 can be set to any postures for better operability.

With the working unit 12a according to the first embodiment, the gripper shaft disposed at the foremost end needs a large torque to produce large gripping forces. With the working unit 12b functioning as an electrosurgical knife, however, the rolling shaft disposed at the foremost end does not need a large torque compared with the gripper shaft. Therefore, priority may be given to the operating range over the torque by setting the number of teeth of the second gear 134≦the number of teeth of the first gear 118. The end effector can thus be actuated in a wider operating range in the rolling directions.

The wider operating range in the rolling directions allows the end effector 304 to be guided to a desired posture from a closer position in either the normal or reverse direction. As the rolling shaft of the end effector 304 can efficiently be guided to a desired posture, the end effector 304 has increased operability.

Figure 18:
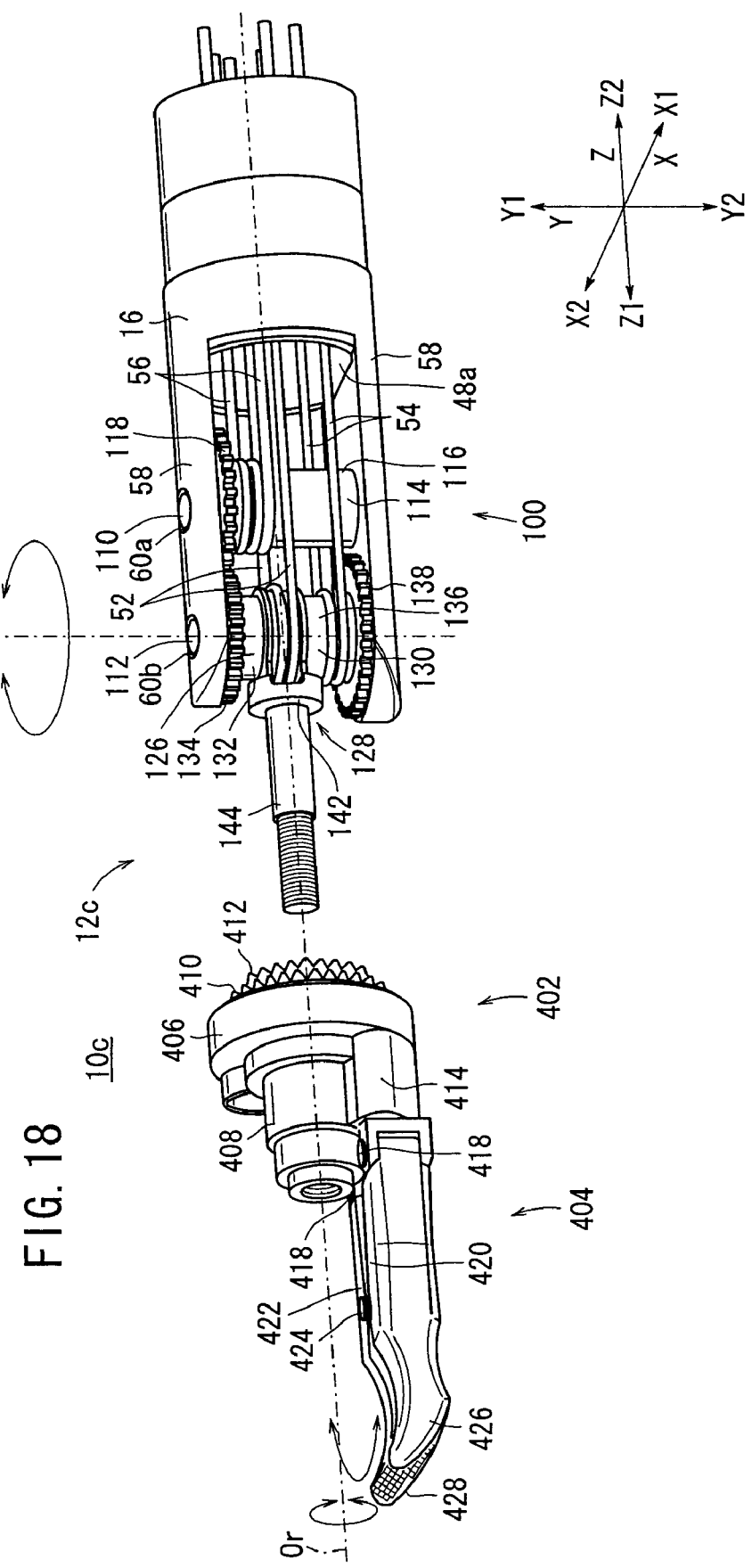
FIG. 18 is an exploded perspective view of the working unit according to the third embodiment.

A manipulator 10c according to a third embodiment of the present invention will be described below with reference to FIGS. 17 and 18. The manipulator 10c has an operation command unit 14 and a connector 16 which are identical to the operation command unit 14 and the connector 16 of the manipulator 10a, and includes a working unit 12c instead of the working unit 12a.

The working unit 12c comprises a wire-driven mechanism 100, a drive mechanism 402, and the end effector 404. The wire-driven mechanism 100 is identical to the wire-driven mechanism 100 of the working unit 12a.

The drive mechanism 402 comprises a flange 406 facing the Z2 direction, a stepped tubular member 408 projection in the Z1 direction from the flange 406, two coaxial face gears 410, 412 disposed on the end of the flange 406 which faces the Z2 direction, and movements 414, 416 actuatable respectively by the face gears 410, 412.

The face gear 410 projects slightly from the surface of the flange 406 and is held in mesh with the third gear 138 of the gear body 130. The face gear 412 is smaller in diameter than the face gear 410 and projects more than the face gear 410. The face gear 412 is held in mesh with the second gear 134 of the gear body 126.

The movements 414, 416, which are symmetrically positioned with respect to a roll axis Or, have respective link supports 418 on their end surfaces which face the Z1 direction. The movements 414, 416 rotate about the tubular member 408, i.e., the roll axis Or, in response to rotation of the face gears 410, 412. The movements 414, 416 operate in coordination under the control of a controller.

The end effector 404 comprises a gripping mechanism including a first member 420 and a second member 422. The first and second members 420, 422 are swingably supported by the respective link supports 418 and extend in the Z1 direction. The first and second members 420, 422 are angularly movably coupled to each other by a substantially intermediate pivot 424.

In the working unit 12c, the movements 414, 416 operate in coordination to turn the end effector 404 about the roll axis Or and to open and close grippers 426, 428 on the distal end portions of the first and second members 420, 422. Specifically, when the movements 414, 416 are moved in the same direction at the same speed, the end effector 404 rotates about the roll axis Or. When the movements 414, 416 are moved in respective directions away from each other, the grippers 426, 428 are actuated in a closing direction. When the movements 414, 416 are moved in respective directions toward each other, the grippers 426, 428 are actuated in an opening direction. The movements 414, 416 may be moved to rotate the end effector 404 about the roll axis Or and open or close the end effector 404 at the same time.

With the working unit 12c, as with the working units 12a, 12b described above, since the wire 56 can be wound in many turns around the tubular member 116, the operating range of at least one of the movements 414, 416 can be set to a large value for thereby widely opening the end effector 404 or rotating the end effector 404 about the roll axis Or through a large operating range.

The first gear 118 and the second gear 134 provide a speed reduction effect to increase a torque for strongly closing the end effector 404 to grip a tool reliably.

It can easily be understood that the grippers 426, 428 of the working unit 12c may be changed in shape and structure into any of various tools including scissors, a pliers, a nipper, an end nipper, etc.

If the speed reduction ratio of the gears is about 1, then in view of the operation about the yaw axis Oy, the roll axis Or, and the gripper axis, it is difficult to achieve an operating range of about ±180° or more around the roll axis Or or achieve an opening and closing angle for the grippers while a certain operating range about the roll axis is being provided.

Wire-driven mechanisms 100a, 100b according to first and second modifications of the wire-driven mechanism 100 of the working units 12a, 12b, 12c will be described below.

Figure 19:
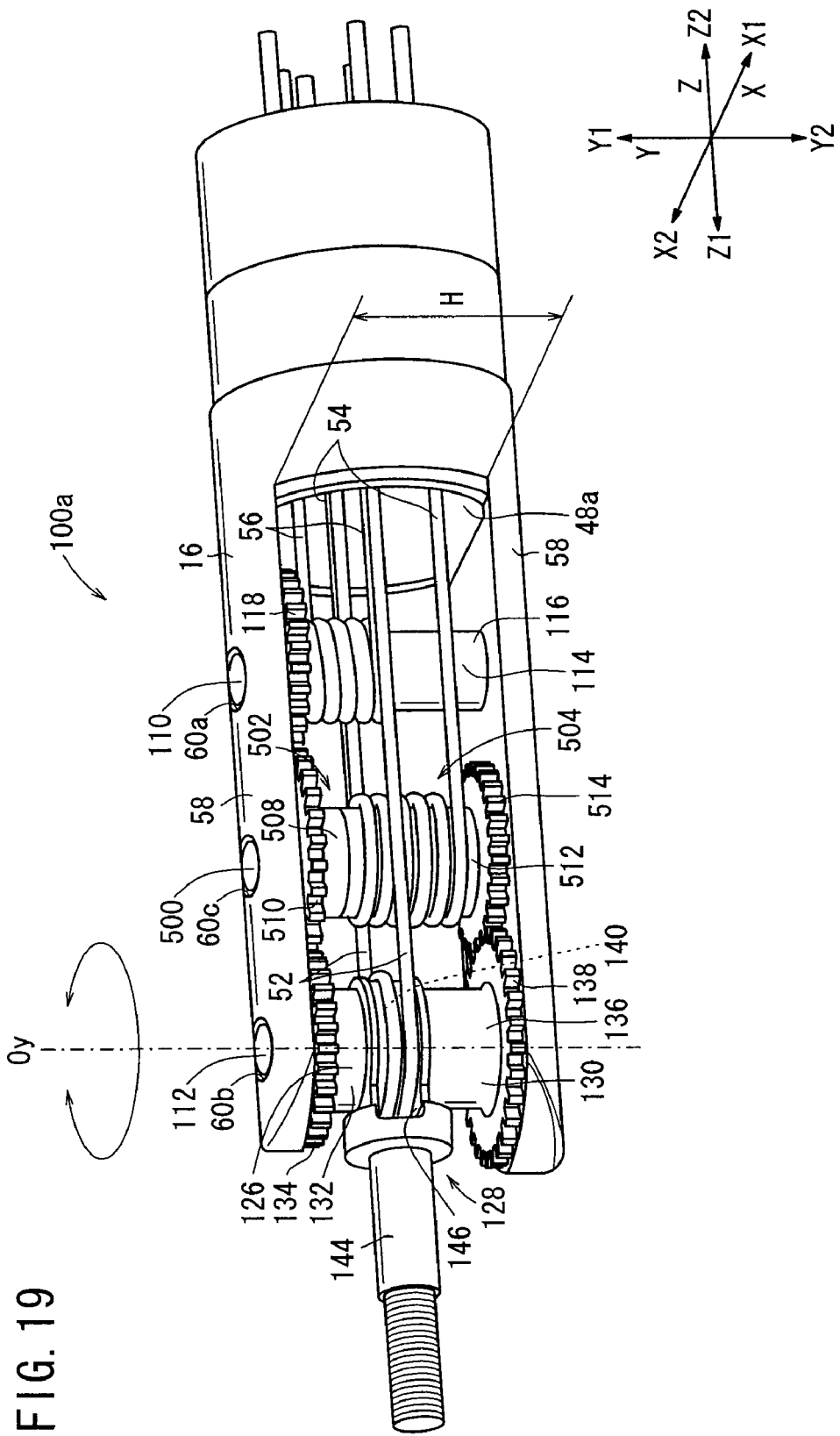
FIG. 19 is a perspective view of a wire-driven mechanism according to a first modification.

As shown in FIG. 19, the wire-driven mechanism 100a according to the first modification includes an intermediate shaft 500 disposed between the shafts 110, 112 which are widely spaced from each other, and two intermediate gear bodies 502, 504 supported on the intermediate shaft 500. The intermediate shaft 500 extends parallel to the shafts 110, 112 and is press-fitted in shaft holes 60c that is defined in the tongues 58 on a line interconnecting the shaft holes 60a, 60b.

The intermediate gear body 502 includes a tubular member 508 and a first intermediate gear (first rotation transmitting mechanism) 510 disposed concentrically on an upper portion of the tubular member 508. The tubular member 508 is larger in diameter than the tubular member 116 and smaller in diameter than the tubular member 140. The first intermediate gear 510 is held in mesh with the first gear 118 at its end in the Z2 direction, and held in mesh with the second gear 134 at its end in the Z1 direction. The first gear 118, the first intermediate gear 510, and the second gear 134 have their numbers of teeth progressively greater in the order named to provide an enhanced speed reduction effect.

The intermediate gear body 504 includes a tubular member (intermediate tubular member) 512 and a second intermediate gear (second rotation transmitting mechanism) 514 disposed concentrically on a lower portion of the tubular member 512. The intermediate gear body 504 is oriented opposite to the intermediate gear body 502 such that the second intermediate gear 514 is in a low position and the tubular member 512 has an end face confronting the end face of the tubular member 508. The tubular member 512 has a height greater than the tubular member 508, and takes up a substantial portion of the distance H between the tongues 58.

The second intermediate gear 514 is held in mesh with the third gear (second rotation transmitting mechanism) 138. The number of teeth of the third gear 138 is greater than the number of teeth of the second intermediate gear 514, so that the second intermediate gear 514 and the third gear 138 provide a speed reduction effect. The wire 54 is wound around the tubular member 512.

The tubular member 512 is larger in diameter than the tubular member 116 and small in diameter than the tubular member 140. More specifically, the tubular member 512 has a diameter set to a value slightly greater than the sum of the diameter of the tubular member 116 and the diameters of two wires 56. As viewed in plan, the wire 54 is disposed slightly outwardly of the wire 56. The tubular member 140 has a diameter set to a value slightly greater than the sum of the diameter of the tubular member 512 and the diameters of two wires 54. As viewed in plan, the wire 52 is disposed slightly outwardly of the wire 54.

In the wire-driven mechanism 100a, as with the working units 12a, 12b, the wire 56 can be wound in many turns around the tubular member 116, allowing the gear body 126 and the end effector ganged with the gear body 126 to operate in an increased operating range. The three-gear assembly of the first gear 118, the first intermediate gear 510, and the second gear 134 provides a speed reduction effect to make the end effector operate reliably.

Since the wire 54 does not interfere with the tubular member 116 offset from the intermediate gear body 504 in the Z2 direction and the tubular member 140 offset from the intermediate gear body 504 in the Z1 direction, and the wire 54 does not interfere with the wires 52, 56 as viewed in plan, the wire 54 can be wound in many turns (e.g., 3.5 turns or more) around the relatively tall tubular member 512. Accordingly, the gear body 130 and the end effector ganged with the gear body 130 can operate in an increased operating range. The second intermediate gear 514 and the third gear 138 provide a speed reduction effect.

Figure 20:
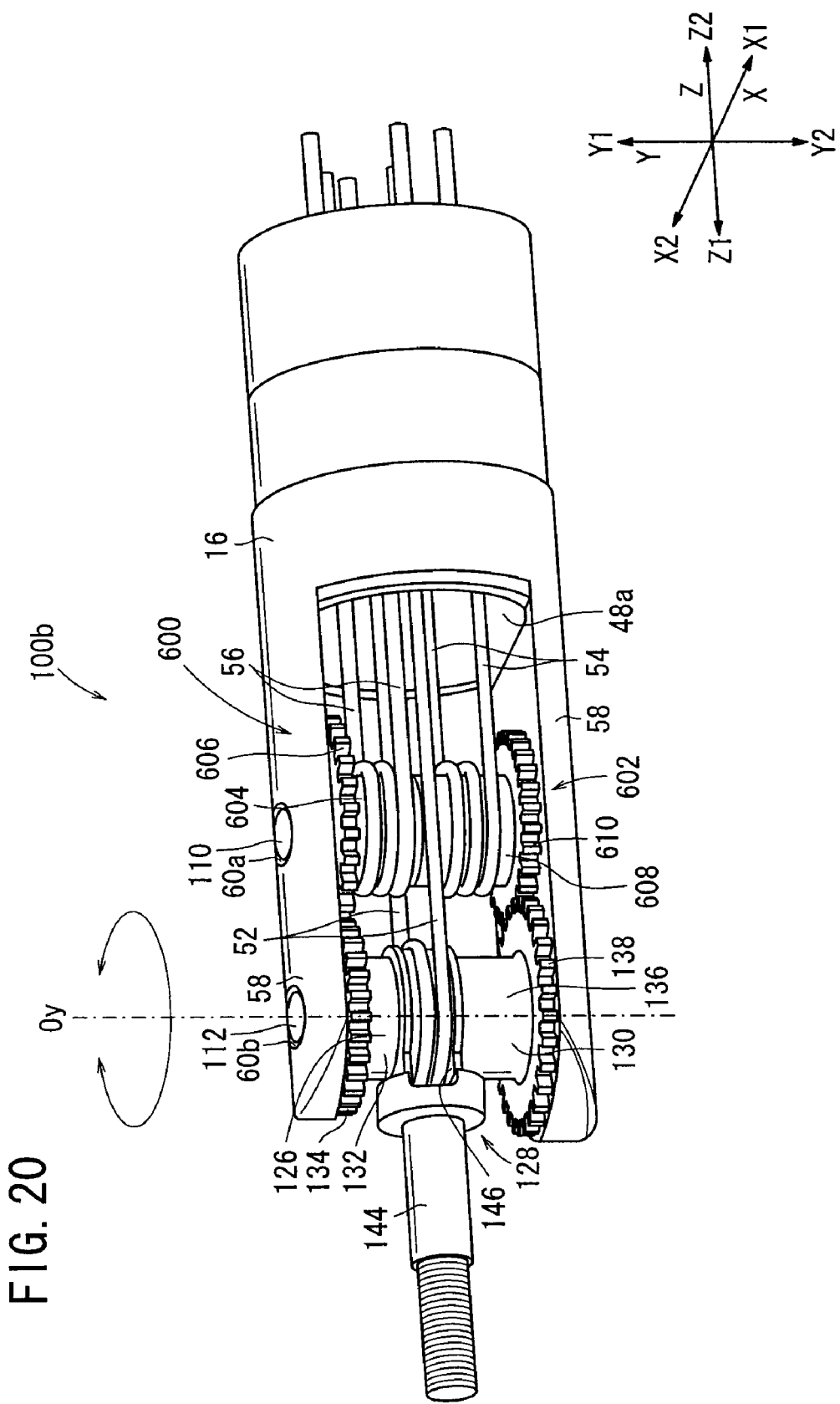
FIG. 20 is a perspective view of a wire-driven mechanism according to a second modification.

As shown in FIG. 20, the wire-driven mechanism 100b according to the second modification includes two gear bodies 600, 602, which are oriented opposite to each other, supported on the shaft 110.

The gear body 600, which corresponds to the gear body 114, includes a tubular member 604 and a first gear 606 disposed concentrically on an upper portion of the tubular member 604. The first gear 606 is identical in shape to the first gear 118. The tubular member 604 is identical in diameter to the tubular member 116 and has a height which is about one-half the height of the tubular member 116.

The gear body 602, which is identical in shape to the gear body 600 and is oriented opposite to the gear body 600, includes a tubular member 608 and a gear 610 that correspond to the tubular member 604 and the first gear 606. The gear body 602 is disposed such that the tubular member 608 has an end face confronting the end face of the tubular member 604. The wire 54 is wound around the tubular member 608. The gear 610 is held in mesh with the third gear 138.

In the wire-driven mechanism 100b, the tubular members 604, 608 are of a shape lower than the tubular member 116, but have a sufficient area for winding many turns of the wires 56, 54. For example, the wires 56, 54 may be wound in about 2.5 turns around the tubular members 604, 608. Therefore, the gear bodies 126, 130 and the end effector ganged therewith can operate in a large operating range.

The gear body 600 and the gear body 602 are disposed coaxially with each other and oriented opposite to each other. The gear body 600 and the gear body 602 share the shaft 110. The gear body 126 and the gear body 130 that are driven by the gear body 600 and the gear body 602 are disposed coaxially with each other and oriented opposite to each other. The gear body 126 and the gear body 130 share the shaft 112. These gear bodies 600, 602, 126, 130 are of a simple structure.

The manipulators 10a, 10b, 10c and the working units 12a, 12b, 12c have been illustrated as being used in the medical application. However, they can also be used in applications to repair narrow regions of energy-related devices and apparatus, and are also applicable to remote control mechanisms for performing techniques on the patient from locations spaced from the patient through electric communication means or the like.

Although certain preferred embodiments of the present invention have been shown and described in detail, it should be understood that various changes and modifications may be made therein without departing from the scope of the appended claims.

What is claimed is:

1. A working mechanism mounted on a distal end of a manipulator for use in laparoscopic surgery, the working mechanism comprising:
    a first flexible power transmitting member;
    a first tubular member, said first flexible power transmitting member being wound around said first tubular member, said first tubular member being rotatable about a first axis;
    a second flexible power transmitting member disposed substantially parallel to said first flexible power transmitting member;
    a second tubular member rotatable about a second axis extending substantially parallel to said first tubular member, said second flexible power transmitting member being wound around said second tubular member;
    a third flexible power transmitting member;
    a third tubular member, said third tubular member being disposed adjacent the second tubular member and rotatable about the third axis the third member is substantially parallel to the first axis and the second axis, said third flexible power transmitting member being wound around said third tubular member;
    a driven rotor having a rotational axis extending substantially parallel to said first tubular member;
    a first rotation transmitting mechanism for transmitting rotation of said first tubular member to said driven rotor;
    a first acting unit operable in an opening and closing direction based on rotation of said driven rotor and the first tubular member rotated by the first flexible power transmitting member; and
    a second acting unit operable in a yawing direction and a rolling direction,
    wherein the second acting unit operates in the yawing direction based on rotation of said second tubular member rotated by the second flexible power transmitting member, and
    the second acting unit operates in the rolling direction based on rotation of the third tubular member rotated by the third flexible power transmitting member.

2. A working mechanism according to claim 1, wherein said first rotation transmitting mechanism comprises a pair of gears.

3. A working mechanism according to claim 1, wherein said second tubular member has a diameter set to a value equal to or greater than a sum of a diameter of said first tubular member and diameters of two of said first flexible power transmitting member.

4. A working mechanism according to claim 1, comprising:
    a plurality of said first flexible power transmitting members;
    a plurality of said driven rotors;
    an intermediate tubular member disposed between said first tubular member and said second tubular member; and
    a second rotation transmitting mechanism for transmitting rotation of said intermediate tubular member to said driven rotors;
    wherein one of said first flexible power transmitting members is wound around said intermediate tubular member.

5. A working mechanism according to claim 1, comprising:
    two of said first flexible power transmitting members;
    two of said first tubular members;
    two of said driven rotors;
    wherein said two of said first tubular members are disposed coaxially with each other and oriented opposite to each other; and
    said two of said driven rotors are disposed coaxially with each other and oriented opposite to each other.

6. A working mechanism according to claim 1, wherein said second tubular member and said driven rotor are disposed coaxially with each other.

7. A working mechanism according to claim 1, further comprising:
    a face gear mounted on said driven rotor;
    a support bar extending from said second tubular member;
    an end effector connected to said support bar; and
    a joint driven gear mounted on said end effector and held in mesh with said face gear;
    wherein when said first flexible power transmitting member circulatively rotates, said first tubular member operates at least one joint of said end effector through said driven rotor, said face gear, and said joint driven gear; and
    when said second flexible power transmitting member circulatively rotates, said second tubular member angularly moves said end effector in a yawing direction.

8. A manipulator for use in laparoscopic surgery including a working mechanism mounted on a distal end thereof, the manipulator comprising:
- a first input member;
- a second input member;
- a first rotational source rotatable in response to operation of said first input member; and
- a second rotational source rotatable in response to operation of said second input member;

the working mechanism comprising:
- a first flexible power transmitting member including a rear portion wound around said first rotational source and a front portion wound in a plurality of turns around a first tubular member;
- the first tubular member, the first flexible power transmitting member being wound around the first tubular member, the first tubular member being rotatable about a first axis,
- a second flexible power transmitting member disposed substantially parallel to said first flexible power transmitting member and extending forwardly on both sides of said first rotational source, said second flexible power transmitting member including a rear portion wound around said second rotational source, said second flexible power transmitting member being wound around a second tubular member disposed forwardly of said first tubular member;
- the second tubular member rotatable about a second axis extending substantially parallel to the first tubular member, the second flexible power transmitting member being wound around the second tubular member;
- a third flexible power transmitting member;
- a third tubular member, said third tubular member being disposed adjacent the second tubular member and rotatable about the second axis the third tubular member is substantially parallel to the first axis and the second axis, said third flexible power transmitting member being wound around said third tubular member;
- a driven rotor disposed forwardly of said first tubular member and having a rotational axis disposed substantially parallel to said first tubular member;
- a rotation transmitting mechanism for transmitting rotation of said first tubular member to said driven rotor;
- a first acting unit operable in an opening and closing direction based on rotation of said driven rotor and the first tubular member rotatable by the first flexible power transmitting member; and
- a second acting unit operable in a yawing direction and a rolling direction,
- wherein the second acting unit operates in the yawing direction based on rotation of said second tubular member rotated by the second flexible power transmitting member, and
- the second acting unit operates in the rolling direction based on rotation of the third tubular member rotated by the third flexible power transmitting member.

* * * * *